(12) United States Patent
Anderson et al.

(10) Patent No.: US 7,252,870 B2
(45) Date of Patent: Aug. 7, 2007

(54) NONWOVENS HAVING REDUCED POISSON RATIO

(75) Inventors: Ralph L. Anderson, Marietta, GA (US); Eugenio G. Varona, Marietta, GA (US); Charles J. Garneski, Kenmore, WA (US); Maurizio Tirimacco, Appleton, WI (US); Douglas W. Stage, Appleton, WI (US); Mark Burazin, Oshkosh, WI (US); Kenneth J. Zwick, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/749,475

(22) Filed: Dec. 31, 2003

(65) Prior Publication Data

US 2005/0142331 A1 Jun. 30, 2005

(51) Int. Cl.
*B32B 3/28* (2006.01)
*B32B 29/08* (2006.01)
*D21H 19/74* (2006.01)
*D21H 19/68* (2006.01)

(52) U.S. Cl. ............. 428/152; 428/153; 428/154; 428/195.1; 428/196; 428/198; 162/111; 162/112

(58) Field of Classification Search ............. 428/152, 428/153, 154, 195.1, 196, 198; 162/111, 162/112
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,494,821 A | 2/1970 | Evans |
| 3,502,538 A | 3/1970 | Petersen |
| 3,502,763 A | 3/1970 | Hartmann |
| 3,542,615 A | 11/1970 | Dobo et al. |

(Continued)

FOREIGN PATENT DOCUMENTS

| | | | |
|---|---|---|---|
| JP | 10-134102 A | * | 5/1998 |
| WO | WO 9101186 A1 | | 2/1991 |
| WO | WO 9932716 A1 | | 7/1999 |
| WO | WO 9934057 A1 | | 7/1999 |
| WO | WO 0066835 A1 | | 11/2000 |

OTHER PUBLICATIONS

Article—*Negative Poisson's Ratio Polymeric and Metallic Foams* adapted from Negative Poisson's ratio polymeric and metallic materials by E. A. Friis, R. S. Lakes, and J. B. Park and published in Journal of Materials Science, vol. 23, 1998, pp. 4406-4414.

(Continued)

*Primary Examiner*—William P. Watkins, III
(74) *Attorney, Agent, or Firm*—Dority & Manning, P.A.

(57) ABSTRACT

Nonwoven materials having a pattern incorporated into the materials are disclosed. The nonwoven materials may be, for instance, tissue webs, meltspun webs such as meltblown webs or spunbond webs, bonded carded webs, hydroentangled webs, and the like. The pattern may be incorporated into the webs using various techniques. For instance, the pattern may be formed into the web by topically applying a bonding material. In an alternative embodiment, the pattern may be formed according to a thermal bonding process. The pattern contains individual cells that include two spaced apart expanded regions separated by a constricted region. By incorporating the pattern into the web, a material is produced having a relatively low Poisson ratio.

46 Claims, 15 Drawing Sheets

U.S. PATENT DOCUMENTS

| | | |
|---|---|---|
| 3,692,618 A | 9/1972 | Dorschner et al. |
| 3,802,817 A | 4/1974 | Matsuki et al. |
| 3,849,241 A | 11/1974 | Butin et al. |
| 3,855,046 A | 12/1974 | Hansen et al. |
| 3,879,257 A | 4/1975 | Gentile et al. |
| 4,100,324 A | 7/1978 | Anderson et al. |
| 4,144,370 A | 3/1979 | Boulton |
| 4,340,563 A | 7/1982 | Appel et al. |
| 4,668,557 A | 5/1987 | Lakes |
| 5,125,659 A | 6/1992 | Garbee |
| 5,129,988 A | 7/1992 | Farrington, Jr. |
| 5,284,703 A | 2/1994 | Everhart et al. |
| 5,350,624 A | 9/1994 | Georger et al. |
| 5,382,400 A | 1/1995 | Pike et al. |
| 5,429,686 A | 7/1995 | Chiu et al. |
| 5,494,554 A | 2/1996 | Edwards et al. |
| 5,529,665 A | 6/1996 | Kaun |
| 5,620,779 A | 4/1997 | Levy et al. |
| 5,656,132 A | 8/1997 | Farrington, Jr. et al. |
| 5,672,248 A | 9/1997 | Wendt et al. |
| 5,962,112 A | 10/1999 | Haynes et al. |
| 6,027,483 A * | 2/2000 | Chappell et al. ....... 604/385.01 |
| 6,093,665 A | 7/2000 | Sayovitz et al. |
| 6,096,169 A | 8/2000 | Hermans et al. |
| 6,103,061 A | 8/2000 | Anderson et al. |
| 6,120,642 A | 9/2000 | Lindsay et al. |
| 6,143,135 A | 11/2000 | Hada et al. |
| 6,197,154 B1 | 3/2001 | Chen et al. |
| 6,197,404 B1 | 3/2001 | Varona |
| 6,315,864 B2 | 11/2001 | Anderson et al. |
| 6,458,447 B1 | 10/2002 | Cabell et al. |

OTHER PUBLICATIONS

Article—*Negative-coefficient materials can point the way to positive value in the right matrixes,* Nancy K. McGuire, Today's Chemist at Work, Nov. 2002, pp. 24-28.

Abstract of Japanese Patent No. JP10134102, May 22, 1998.

PCT Search Report and Written Opinion for PCT/US2004/038215.

* cited by examiner

NONWOVENS HAVING REDUCED POISSON RATIO

BACKGROUND OF THE INVENTION

Many nonwoven sheet materials, such as tissue webs, meltspun webs, hydroentangled webs, bonded carded webs, and the like are designed to include several important properties. For example, tissue products should have good bulk, a soft feel and should be highly absorbent. Tissue products should also have good strength even while wet and should resist tearing. Unfortunately, it is very difficult to produce a high strength tissue product that is also soft and highly absorbent. Usually, when steps are taken to increase one property of the product, other characteristics of the product are adversely affected. For instance, softness is typically increased by decreasing or reducing fiber bonding within the tissue product. Inhibiting or reducing fiber bonding, however, adversely affects the strength of the tissue web.

In the past, various methods have been used in order to increase the strength of nonwoven webs. For instance, many tissue webs and meltspun webs, such as meltblown webs and spunbond webs, undergo embossing or thermal bonding after being formed in order to increase the strength and integrity of the webs. In many applications, the web is thermally bonded according to a particular pattern. Nonwoven webs are also treated with latex materials to increase strength. The latex materials may be applied topically to the web in a pattern.

One particular process that has proved to be very successful in increasing the strength of tissue products, such as paper towels and wipers, without significantly adversely affecting other properties of the web is disclosed in U.S. Pat. No. 3,879,257 to Gentile, et al., which is incorporated herein by reference. In Gentile, et al., a process is disclosed in which a bonding material is applied in a fine, spaced apart pattern to one side of a fibrous web. The web is then adhered to a heated creping surface and creped from the surface. A bonding material is applied to the opposite side of the web and the web is similarly creped. The process disclosed in Gentile, et al. produces tissue products having exceptional bulk, outstanding softness and good absorbency. The surface regions of the web also provide excellent strength, abrasion resistance, and wipe-dry properties.

One problem that still persists, however, is the ability to produce a web that has properties in the cross-machine direction that are comparable to the properties of the web in the machine direction. For instance, many of the bonding patterns that are applied to webs typically greatly enhance the strength and stretch properties of the web in the machine direction without similarly increasing the same properties of the web in the cross-machine direction.

One particular problem encountered in the manufacture of nonwoven sheet materials is that most materials exhibit relatively high Poisson ratios in that when the material is pulled in the machine direction, the width of the material in the cross-machine direction significantly decreases. Since nonwoven materials are typically pulled in the machine direction during formation of the materials and during incorporation of the materials into a product, the above effect must be compensated for when processing the nonwoven materials. In some applications, the machine width is overdesigned or process conditions are compromised in order to control the width loss. This problem also extends into finishing operations causing issues of sheet control and overcompensating machine conditions or product dimensions.

As such, a need currently exists for a method of improving the overall properties of nonwoven sheet materials. In particular, a need currently exists for nonwoven sheet materials having a bonding pattern that reduces the Poisson ratio of the material such that the material has less tendency to shrink in the cross-machine direction when pulled in the machine direction.

A need also exists for an improved tissue product that possesses a negative Poisson ratio. When having a negative Poisson ratio, the web actually increases in width when the material is pulled in the lengthwise direction. It is believed that by creating a tissue product with a negative Poisson ratio, the product will also exhibit an increase in stretch in the cross-machine direction, with increased energy absorption in the cross direction.

SUMMARY OF THE INVENTION

In general, the present invention is directed to a method for producing nonwoven sheet materials and to sheet materials made from the method. In one particular embodiment of the present invention, for instance, a tissue product is formed similar to the process disclosed in Gentile, et al. as described above. For instance, in this embodiment, a bonding material is applied to the first side of a tissue web according to a preselected pattern. The pattern comprises a plurality of individual cells. Each cell comprises first and second expanded regions connected together by a constricted region. The individual cells may be interconnected along at least two sides to adjacent cells. For instance, in one embodiment, every side of each cell is interconnected with an adjacent cell. After the bonding material is applied to the first side of the tissue web, the first side of the tissue web is creped. For example, the tissue web may be adhered to a creping surface and then creped from the surface.

If desired, a second bonding material may be applied to the second side of the tissue web according to a similar pattern. The second side of the tissue web may also be optionally creped, depending upon the particular application. The bonding materials may be, for instance, an ethylene vinyl acetate copolymer.

The pattern by which the bonding material is applied as described above reduces the Poisson ratio of the tissue web. In one embodiment, for instance, it is believed that the tissue web may actually have a negative Poisson ratio. In other embodiments, the tissue web may have a Poisson ratio of less than about 0.3, such as less than about 0.25, less than about 0.2, or less than about 0.1.

The individual cells that make up the pattern may have a variety of shapes. For instance, the expanded regions may have a square, triangular, hexagonal, elliptical or curvilinear shape. The constricted region may have a width of less than about 2 mm, such as less than about 1.5 mm. For instance, in one embodiment, the constricted region has a width of from about 0.5 mm to about 1.5 mm, such as about 0.75 mm.

The tissue web may have a basis weight of from about 10 gsm to about 120 gsm, such as from about 20 gsm to about 80 gsm. In general, however, lowering the basis weight of the tissue web may lead to much lower Poisson ratios, such as negative Poisson ratios, particularly, when the internal fiber bonding is disrupted by use of a cellulose debonder, e.g. Arosurf PA801 (available from Degussa-Goldschmidt Chem. Corp.). When producing tissue webs having a negative Poisson ratio, for instance, the tissue web may have a basis weight of less than about 40 gsm, such as less than about 30 gsm.

The tissue web after being creped may have a bulk greater than about 2 cc/g, such as greater than about 5 cc/g. In other embodiments, the bulk of the tissue web may be greater than about 9 cc/g, such as greater than about 10 cc/g, such as greater than about 11 cc/g. For instance, in one embodiment, the tissue web may have a bulk of from about 9 cc/g to about 12 cc/g.

The tissue web as described above may be incorporated into various tissue products. For instance, the tissue web may be used to produce paper towels, industrial wipers, facial tissues, bath tissues, napkins, and the like.

In addition to forming tissue products according to a print creping process, patterns as described above may be incorporated into various nonwoven sheet materials using various techniques for reducing Poisson ratios. The nonwoven sheet materials may be, in addition to tissue webs, meltspun webs such as meltblown webs or spunbond webs, hydroentangled webs, bonded carded webs, and the like. Once formed, the nonwoven sheet materials may be incorporated into laminates or may be used in a single ply product. Almost an infinite variety of products may be formed from the sheet materials in addition to the tissue products described above. For instance, nonwoven sheet materials made according to the present invention can be used to produce absorbent articles such as diapers, feminine hygiene products, adult incontinence products, absorbent swimwear, surgical drapes, bandages, and the like.

Patterns as described above may be formed into the nonwoven sheet materials using various methods in addition to print creping processes. For instance, the pattern may be thermally bonded into the web. In this embodiment, for instance, the web may be fed through a heated embossing roll which forms the pattern.

In another embodiment, the pattern may be formed into the nonwoven web by forming the web on a forming surface having a 3-dimensional topography that contains a pattern as described above. When formed on the forming surface, the pattern becomes incorporated into the web. The forming surface may be, for instance, a fabric where water drainage occurs or a drying fabric should the nonwoven web comprise a tissue web. Alternatively, the nonwoven web may be formed on a forming fabric having differential drainage to impart a pattern of high and low basis weights corresponding to a pattern as described above. In still another embodiment, the nonwoven web may be a tissue web that is molded into a drying fabric imparting a 3-dimensional topography to the tissue web that contains a pattern as described above, optionally drying the web to final dryness while the tissue web is held in the 3-dimensional state.

In another embodiment of the present invention, a laminated structure may be produced having a relatively low Poisson ratio. The laminated structure may comprise one or more auxetic layers in accordance with the present invention. The auxetic layer, for instance, may comprise a scrim or apertured film in which the openings in the material comprise an auxetic pattern.

Various other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
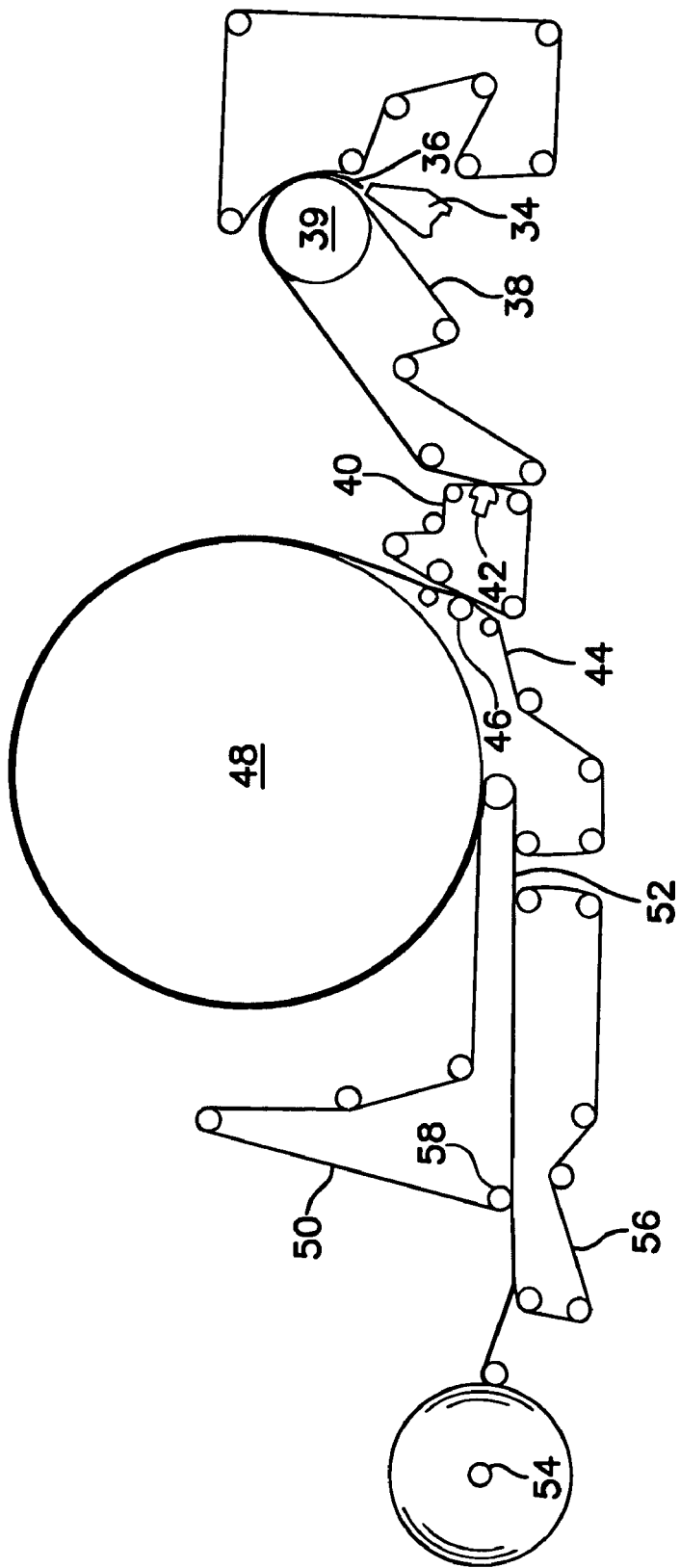
FIG. 1 is a schematic diagram of one embodiment of a process for forming uncreped through-dried tissue webs for use in the present invention.

Repeat use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention.

In general, the present invention is directed to various nonwoven sheet materials that have improved properties due to the incorporation of a pattern into the materials. The pattern may comprise a plurality of individual cells. The cells may be interconnected. Each cell includes first and second expanded regions connected together by a constricted region. Examples of patterns according to the present invention, for instance, are shown in FIGS. 5, 7, 8, 9, 10, and 11.

In accordance with the present invention, the pattern incorporated into the nonwoven material significantly lowers the Poisson ratio of the material. The Poisson ratio of a material is the ratio of transverse contraction strain to longitudinal extension strain in the direction of a stretching force. Tensile deformation is considered positive and compressive deformation is considered negative. The mathematical expression of a Poisson ratio for a material contains a minus sign so that normal materials have a positive ratio. In other words, since most common materials decrease in width when stretched in a lengthwise direction, the Poisson ratio for these materials is positive.

When a pattern of the present invention is incorporated into a nonwoven material, the Poisson ratio of the material is significantly reduced. The pattern causes the material to resist deformation and shrinkage of the width of the material when the material is pulled in the lengthwise direction. Specifically, with a negative Poisson ratio, the constricted regions of the individual cells contained in the pattern expand when the material is pulled in an opposite direction. In this manner, the cells may be considered to be auxetic (growing), since the cells expand when subjected to strain.

In certain embodiments of the present invention, especially when processing tissue webs according to a print creping process, the auxetic pattern may in fact create a tissue web having a negative Poisson ratio. When the material has a negative Poisson ratio, the material actually increases in width when stretched in the lengthwise direction. Tissue webs exhibiting a negative Poisson ratio may display increased cross-direction stretch and increased energy absorption in the cross direction.

During a print creping process, a first bonding material is applied to a first side of a base sheet or tissue web. The first side of the tissue web is then adhered to a creping surface and creped from the surface. Optionally, a second bonding material, which can be the same or different from the first bonding material, may be applied according to a preselected pattern to the second side of the tissue web. The second side of the tissue web may then be creped if desired.

In accordance with the present invention, the bonding materials are applied to the tissue web in preselected patterns that create a product having a relatively low Poisson ratio such as a negative Poisson ratio, provided the fiber to fiber bonding is reduced enough to allow the pattern bonding to be predominant. Creping the web causes delamination and increases the sheet caliper and cross-directional stretch of the web. By increasing caliper, creping also increases the bulk of the sheet making the tissue web feel softer.

Exemplary embodiments of print creping processes will now be described in detail. It should be understood, however, that a print creping process is merely one exemplary embodiment for use of the patterns of the present invention. In no way is the following description intended to limit the invention.

Tissue webs processed according to the present invention can be made in different manners and can contain various different types of fibers. In general, however, the tissue web contains papermaking fibers, such as softwood fibers. In addition to softwood fibers, the tissue web can also contain hardwood fibers such as eucalyptus fibers and/or high-yield pulp fibers. In a preferred embodiment, the tissue web is produced from northern softwood fibers of a coarseness of 11-15, with a fiber length of 2-3 mm.

As used herein, "high-yield pulp fibers" are those papermaking fibers produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. Such pulping processes include bleached chemithermomechanical pulp (BCTMP), chemithermomechanical pulp (CTMP) pressure/pressure thermomechanical pulp (PTMP), thermomechanical pulp (TMP), thermomechanical chemical pulp (TMCP), high-yield sulfite pulps, and high-yield kraft pulps, all of which leave the resulting fibers with high levels of lignin. High-yield fibers are well known for their stiffness (in both dry and wet states) relative to typical chemically pulped fibers. The cell wall of kraft and other non-high-yield fibers tends to be more flexible because lignin, the "mortar" or "glue" on and in part of the cell wall, has been largely removed. Lignin is also nonswelling in water and hydrophobic, and resists the softening effect of water on the fiber, maintaining the stiffness of the cell wall in wetted high-yield fibers relative to kraft fibers. The preferred high-yield pulp fibers can also be characterized by being comprised of comparatively whole, relatively undamaged fibers, high freeness (250 Canadian Standard Freeness (CSF) or greater, more specifically 350 CFS or greater, and still more specifically 400 CFS or greater), and low fines content (less than 25 percent, more specifically less than 20 percent, still more specifically less that 15 percent, and still more specifically less than 10 percent by the Britt jar test).

In one embodiment of the present invention, the tissue web contains softwood fibers in combination with high-yield pulp fibers, particularly BCTMP fibers. BCTMP fibers can be added to the web in order to increase the bulk and caliper of the web, while also reducing the cost of the web.

The amount of high-yield pulp fibers present in the sheet can vary depending upon the particular application. For instance, the high-yield pulp fibers can be present in an amount of about 2 dry weight percent or greater, particularly about 15 dry weight percent or greater, and more particularly from about 5 dry weight percent to about 40 dry weight percent, based upon the total weight of fibers present within the web.

In one embodiment, the tissue web can be formed from multiple layers of a fiber furnish. The tissue web can be produced, for instance, from a stratified headbox. Layered structures produced by any means known in the art are within the scope of the present invention, including those disclosed in U.S. Pat. No. 5,494,554 to Edwards, et al. and U.S. Pat. No. 5,129,988 to Farrington, which are incorporated herein by reference.

In one embodiment, for instance, a layered or stratified web is formed that contains high-yield pulp fibers in the center. Because high-yield pulp fibers are generally less soft than other papermaking fibers, in some applications, it is advantageous to incorporate them into the middle of the tissue web, such as by being placed in the center of a 3-layered sheet. The outer layers of the sheet can then be made from softwood fibers and/or hardwood fibers.

For example, in one particular embodiment of the present invention, the tissue web contains outer layers made from softwood fibers. Each outer layer can comprise from about 15% to about 40% by weight of the web and particularly can comprise about 25% by weight of the web. The middle layer, however, can comprise from about 40% to about 60% by weight of the web, and particularly about 50% by weight of the web. The middle layer can contain a mixture of softwood fibers and BCTMP fibers. The BCTMP fibers can be present in the middle layer in an amount from about 40% to about 60% by weight of the middle layer, and particularly in an amount of about 50% by weight of the middle layer.

In another embodiment of the present invention, the tissue web can be made containing two layers of fibers. The first layer can contain the high-yield pulp fibers. The second layer, on the other hand, can comprise softwood fibers. This particular embodiment is well suited for creating two-ply products. In particular, the layer of fibers containing the high-yield fibers can be laminated to a second nonwoven web in forming the multi-ply product. The layer of fibers containing the softwood fibers, on the other hand, may be treated with a bonding material and creped from a creping surface.

The tissue web of the present invention can also be formed without a substantial amount of inner layer fiber-to-fiber bond strength. In this regard, the fiber furnish used to form the base web can be treated with a chemical debonding agent. The debonding agent can be added to the fiber slurry during the pulping process or can be added directly into the head box. Suitable debonding agents that may be used in the present invention include cationic debonding agents such as fatty dialkyl quaternary amine salts, mono fatty alkyl tertiary amine salts, primary amine salts, imidazoline quaternary salts, silicone quaternary salt and unsaturated fatty alkyl amine salts. Other suitable debonding agents are disclosed in U.S. Pat. No. 5,529,665 to Kaun which is incorporated herein by reference. In particular, Kaun discloses the use of cationic silicone compositions as debonding agents.

In one embodiment, the debonding agent used in the process of the present invention is an organic quaternary ammonium chloride and particularly a silicone based amine salt of a quaternary ammonium chloride. For example, the debonding agent can be PROSOFT TQ1003 marketed by the Hercules Corporation. The debonding agent can be added to the fiber slurry in an amount of from about 1 kg per metric tonne to about 10 kg per metric tonne of fibers present within the slurry.

In an alternative embodiment, the debonding agent can be an imidazoline-based agent. The imidazoline-based debonding agent can be obtained, for instance, from the Witco Corp. of Middlebury, Conn. The imidazoline-based debonding agent can be added in an amount of between 2.0 to about 15 kg per metric tonne.

In one embodiment, the debonding agent can be added to the fiber furnish according to a process as disclosed in PCT Application having an International Publication No. WO 99/34057 filed on Dec. 17, 1998 or in PCT Published Application having an International Publication No. WO 00/66835 filed on Apr. 28, 2000, which are both incorporated herein by reference. In the above publications, a process is disclosed in which a chemical additive, such as a debonding agent, is adsorbed onto cellulosic papermaking fibers at high levels. The process includes the steps of treating a fiber slurry with an excess of the chemical additive, allowing sufficient residence time for adsorption to occur, filtering the slurry to remove unadsorbed chemical additives, and redispersing the filtered pulp with fresh water prior to forming a nonwoven web.

The basis weight of tissue webs used in the process of the present invention can vary depending upon the final product. For example, the process of the present invention can be used to produce bath or facial tissue webs, paper towels, industrial wipers, and the like. For these products, the basis weight of the tissue web can vary from about 10 gsm to about 120 gsm, and particularly from about 20 gsm to about 80 gsm.

In multiple ply products, the basis weight of each tissue web present in the product can also vary. In general, the total basis weight of a multiple ply product will generally be the same as indicated above, such as from about 10 gsm to about 120 gsm. Thus, the basis weight of each ply can be from about 10 gsm to about 60 gsm, such as from about 15 gsm to about 40 gsm.

As stated above, the manner in which the tissue web is formed can also vary depending upon the particular application. In general, the tissue web can be formed by any of a variety of papermaking processes known in the art. For example, the tissue web can be a wet-creped web, a calendered web, an embossed web, a through-air dried web, a creped through-air dried web, an uncreped through-air dried web, as well as various combinations of the above. In one particular embodiment of the present invention, however, the tissue web is made in an uncreped through-air dried process.

For example, referring to FIG. 1, shown is a method for making throughdried paper sheets in accordance with this invention. (For simplicity, the various tensioning rolls schematically used to define the several fabric runs are shown but not numbered. It will be appreciated that variations from the apparatus and method illustrated in FIG. 1 can be made without departing from the scope of the invention.) Shown is a twin wire former having a papermaking headbox 34, such as a layered headbox, which injects or deposits a stream 36 of an aqueous suspension of papermaking fibers onto the forming fabric 38 positioned on a forming roll 39. The forming fabric serves to support and carry the newly-formed wet web downstream in the process as the web is partially dewatered to a consistency of about 10 dry weight percent. Additional dewatering of the wet web can be carried out, such as by vacuum suction, while the wet web is supported by the forming fabric.

The wet web is then transferred from the forming fabric to a transfer fabric 40. In one embodiment, the transfer fabric can be traveling at a slower speed than the forming fabric in order to impart increased stretch into the web. This is commonly referred to as a "rush" transfer. The transfer fabric can have a void volume that is equal to or less than that of the forming fabric. The relative speed difference between the two fabrics can be from 0-60 percent, more specifically from about 15-45 percent. Transfer is preferably carried out with the assistance of a vacuum shoe 42 such that the forming fabric and the transfer fabric simultaneously converge and diverge at the leading edge of the vacuum slot.

The web is then transferred from the transfer fabric to the throughdrying fabric 44 with the aid of a vacuum transfer roll 46 or a vacuum transfer shoe, optionally again using a fixed gap point contact transfer as previously described. The throughdrying fabric can be traveling at about the same speed or a different speed relative to the transfer fabric. If desired, the throughdrying fabric can be run at a slower speed to further enhance stretch. Transfer can be carried out with vacuum assistance to ensure deformation of the sheet to conform to the throughdrying fabric, thus yielding desired bulk and appearance if desired. Suitable throughdrying fabrics are described in U.S. Pat. No. 5,429,686 issued to Kai F. Chiu et al. and U.S. Pat. No. 5,672,248 to Wendt. et al. which are incorporated by reference.

In one embodiment, the throughdrying fabric contains high and long impression knuckles. For example, the throughdrying fabric can have about from about 5 to about 300 machine direction impression knuckles per square inch which are raised at least about 0.005 inches above the plane of the fabric. During drying, the web can be macroscopically arranged to conform to the surface of the throughdrying fabric and form a three-dimensional surface. Flat surfaces, however, can also be used in the present invention.

The side of the web contacting the throughdrying fabric is typically referred to as the "fabric side" of the tissue web. The fabric side of the tissue web, as described above, may have a shape that conforms to the surface of the throughdrying fabric after the fabric is dried in the throughdryer. The opposite side of the tissue web, on the other hand, is typically referred to as the "air side". The air side of the web is typically smoother than the fabric side during normal throughdrying processes.

The level of vacuum used for the web transfers can be from about 3 to about 15 inches of mercury (about 75 to about 380 millimeters of mercury), preferably about 5 inches (about 125 millimeters) of mercury. The vacuum shoe (negative pressure) can be supplemented or replaced by the use of positive pressure from the opposite side of the web to blow the web onto the next fabric in addition to or as a replacement for sucking it onto the next fabric with vacuum. Also, a vacuum roll or rolls can be used to replace the vacuum shoe(s).

While supported by the throughdrying fabric, the web is final dried to a consistency of about 94 percent or greater by the throughdryer 48 and thereafter transferred to a carrier fabric 50. The dried basesheet 52 is transported to the reel 54 using carrier fabric 50 and an optional carrier fabric 56. An optional pressurized turning roll 58 can be used to facilitate transfer of the web from carrier fabric 50 to fabric 56. Suitable carrier fabrics for this purpose are Albany International 84M or 94M and Asten 959 or 937, all of which are relatively smooth fabrics having a fine pattern. Although not shown, reel calendering or subsequent off-line calendering can be used to improve the smoothness and softness of the basesheet.

In one embodiment, the tissue web 52 is a textured web which has been dried in a three-dimensional state such that the hydrogen bonds joining fibers were substantially formed while the web was not in a flat, planar state. For instance, the web can be formed while the web is on a highly textured throughdrying fabric or other three-dimensional substrate. Processes for producing uncreped throughdried fabrics are, for instance, disclosed in U.S. Pat. No. 5,672,248 to Wendt, et al.; U.S. Pat. No. 5,656,132 to Farrington, et al.; U.S. Pat. No. 6,120,642 to Lindsay and Burazin; U.S. Pat. No. 6,096,169 to Hermans. et al.; U.S. Pat. No. 6,197,154 to Chen, et al.; and U.S. Pat. No. 6,143,135 to Hada, et al., all of which are herein incorporated by reference in their entireties.

Uncreped through-air dried tissue webs made according to the process illustrated in FIG. 1 may provide various advantages in the process of the present invention. It should be understood, however, that other types of tissue webs can be used in the present invention. For example, in an alternative embodiment, a wet creped tissue web can be utilized.

Figure 2:
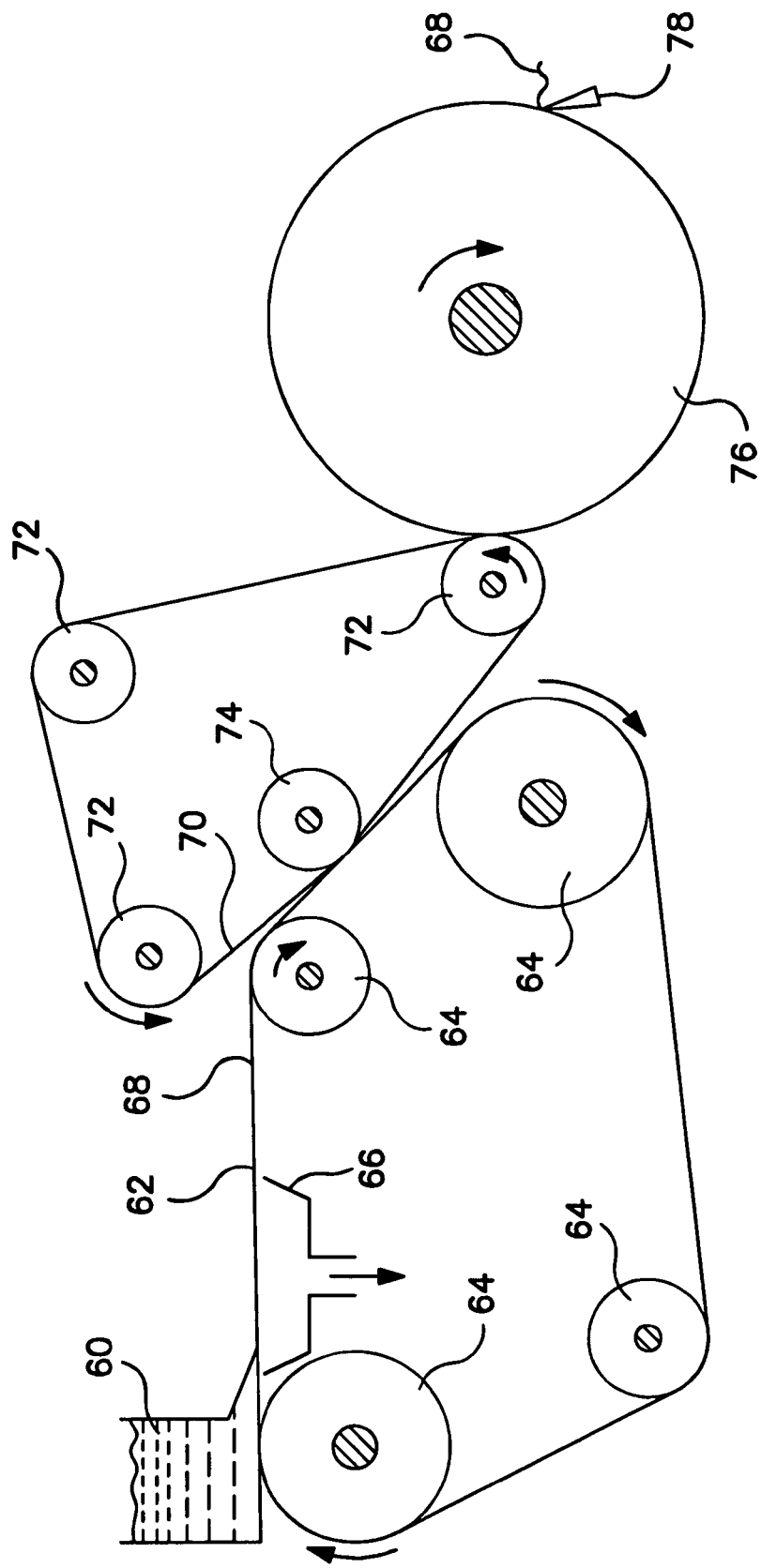
FIG. 2 is a schematic diagram of one embodiment of a process for forming wet creped tissue webs for use in the present invention.

For example, referring to FIG. 2, one embodiment of a papermaking machine is illustrated capable of forming a tissue web for use in the process of the present invention. As shown, in this embodiment, a head box 60 emits an aqueous suspension of fibers onto a forming fabric 62 which is supported and driven by a plurality of guide rolls 64. A vacuum box 66 is disposed beneath forming fabric 62 and is adapted to remove water from the fiber furnish to assist in forming a web. From forming fabric 62, a formed web 68 is transferred to a second fabric 70, which may be either a wire or a felt. Fabric 70 is supported for movement around a continuous path by a plurality of guide rolls 72. Also included is a pick up roll 74 designed to facilitate transfer of web 68 from fabric 62 to fabric 70.

From fabric 70, web 68, in this embodiment, is transferred to the surface of a rotatable heated dryer drum 76, such as a Yankee dryer. Web 68 is lightly pressed into engagement with the surface of dryer drum 76 to which it adheres, due to its moisture content and its preference for the smoother of the two surfaces. In some cases, however, an adhesive can be applied over the web surface or drum surface for facilitating attachment of the web to the drum.

As web 68 is carried through a portion of the rotational path of the dryer surface, heat is imparted to the web causing most of the moisture contained within the web to be evaporated. Web 68 is then removed from dryer drum 76 by a creping blade 78. Although optional, creping web 68 as it is formed further reduces internal bonding within the web and increases softness.

Figure 3:
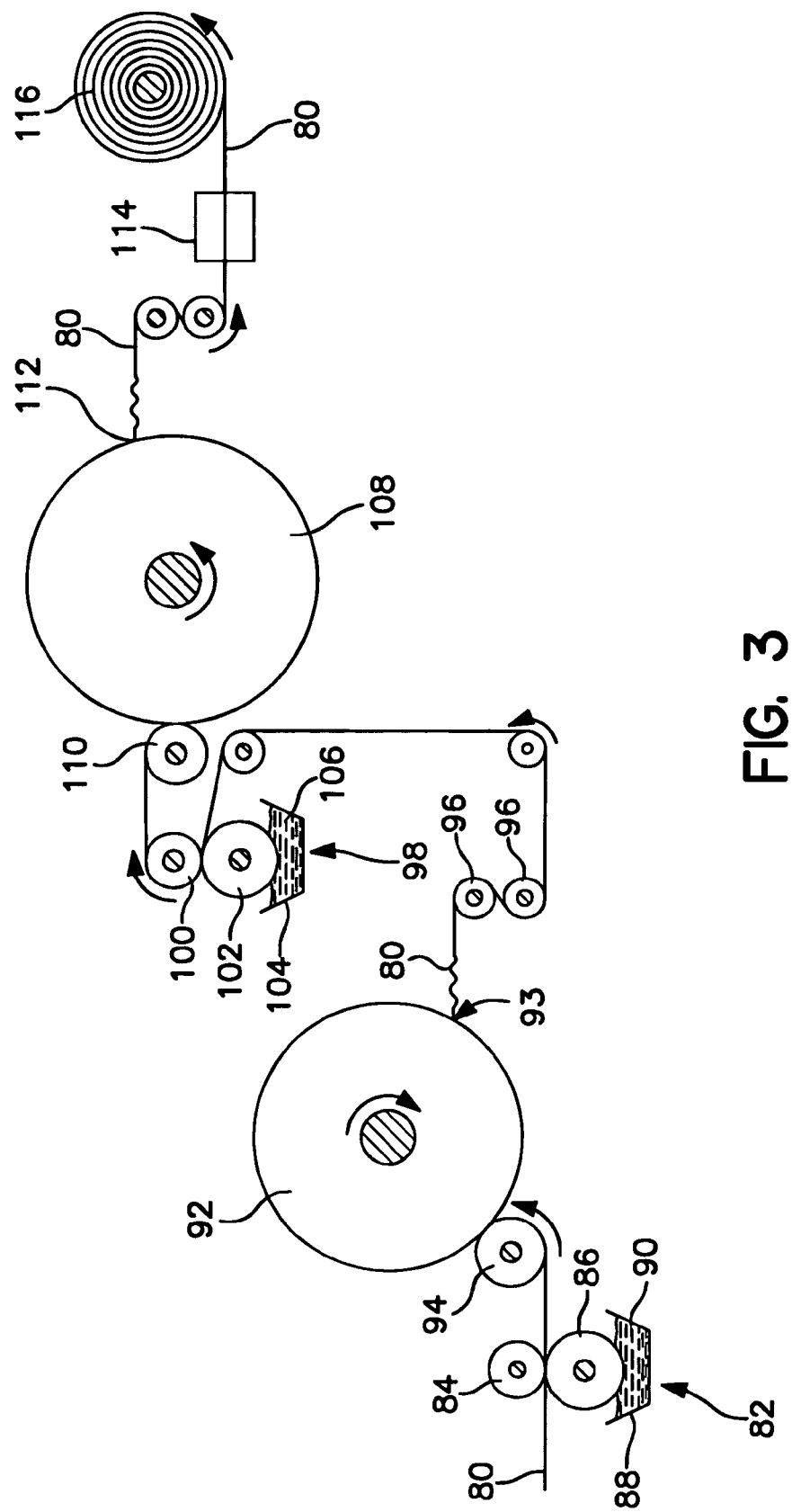
FIG. 3 is a schematic diagram of one embodiment of a process for applying bonding materials to each side of a tissue web and creping of the web in accordance with the present invention.

Once the tissue web is formed, a bonding material is applied to at least one side of the web according to a pattern of the present invention and at least one side of the web is then creped. Referring to FIG. 3, one embodiment of a system that may be used to apply bonding materials to each side of the tissue web and to crepe each side of the web is illustrated. The embodiment shown in FIG. 3 can be an in-line or off-line process. As shown, tissue web 80 made according to the process illustrated in FIG. 1 or FIG. 2 or according to a similar process, is passed through a first bonding agent application station generally 82. Station 82 includes a nip formed by a smooth rubber press roll 84 and a patterned rotogravure roll 86. Rotogravure roll 86 is in communication with a reservoir 88 containing a first bonding material 90. Rotogravure roll 86 applies the bonding material 90 to one side of web 80 in a preselected pattern according to the present invention.

Web 80 is then contacted with a heated creping roll 92 by a press roll 94. The tissue web 80 is carried on the surface of the creping roll 92 for a distance and then removed therefrom by the action of a creping blade 93. The creping blade 93 performs a controlled pattern creping operation on the first side of the tissue web.

From the creping roll 92, the web 80 can be advanced by pull rolls 96 to a second bonding material application station generally 98. Station 98 includes a transfer roll 100 in contact with a rotogravure roll 102, which is in communication with a reservoir 104 containing a second bonding material 106. Similar to station 82, second bonding material 106 is applied to the opposite side of web 80 in a preselected pattern according to the present invention. Once the second bonding material is applied, web 80 is adhered to a heated creping roll 108 by a press roll 110. Web 80 is carried on the surface of the creping drum 108 for a distance and then removed therefrom by the action of a creping blade 112. The creping blade 112 performs a controlled pattern creping operation on the second side of the tissue web.

Once creped, tissue web 80, in this embodiment, is pulled through a drying station 114. Drying station 114 can include any form of a heating unit, such as an oven energized by infrared heat, microwave energy, hot air or the like. Drying station 114 may be necessary in some applications to dry the web and/or cure the bonding materials. Depending upon the bonding materials selected, however, in other applications drying station 114 may not be needed.

Once passed through drying station 114, web 80 can be wound into a roll of material 116.

The bonding materials applied to each side of the tissue web are selected for not only assisting in creping the web but also for adding dry strength, wet strength, stretchability, and tear resistance to the paper. Particular bonding materials that may be used in the present invention include latex compositions, such as acrylates, vinyl acetates, vinyl chlorides and methacrylates. Some water-soluble bonding materials may also be used including carboxylated vinyl acetate-ethylene terpolymers, polyacrylamides, polyvinyl alcohols and cellulose derivatives such as carboxymethyl cellulose. In one embodiment, the bonding materials used in the process of the present invention comprise an ethylene vinyl acetate copolymer. In particular, the ethylene vinyl acetate copolymer can be cross-linked with N-methyl acrylamide groups using an acid catalyst. Suitable acid catalysts include ammonium chloride, citric acid and maleic acid. Examples of such bonding materials are produced by Air Products Corporation.

In general, the first bonding material and the second bonding material can be different bonding materials or the same bonding material.

The bonding materials are applied to the base web as described above in preselected patterns. The patterns of the present invention create a tissue web having a significantly reduced Poisson ratio. In particular, once a pattern according to the present invention is applied to a tissue web, the pattern counteracts the natural tendency of the web to shrink during creping, drying or pulling.

Figure 5:
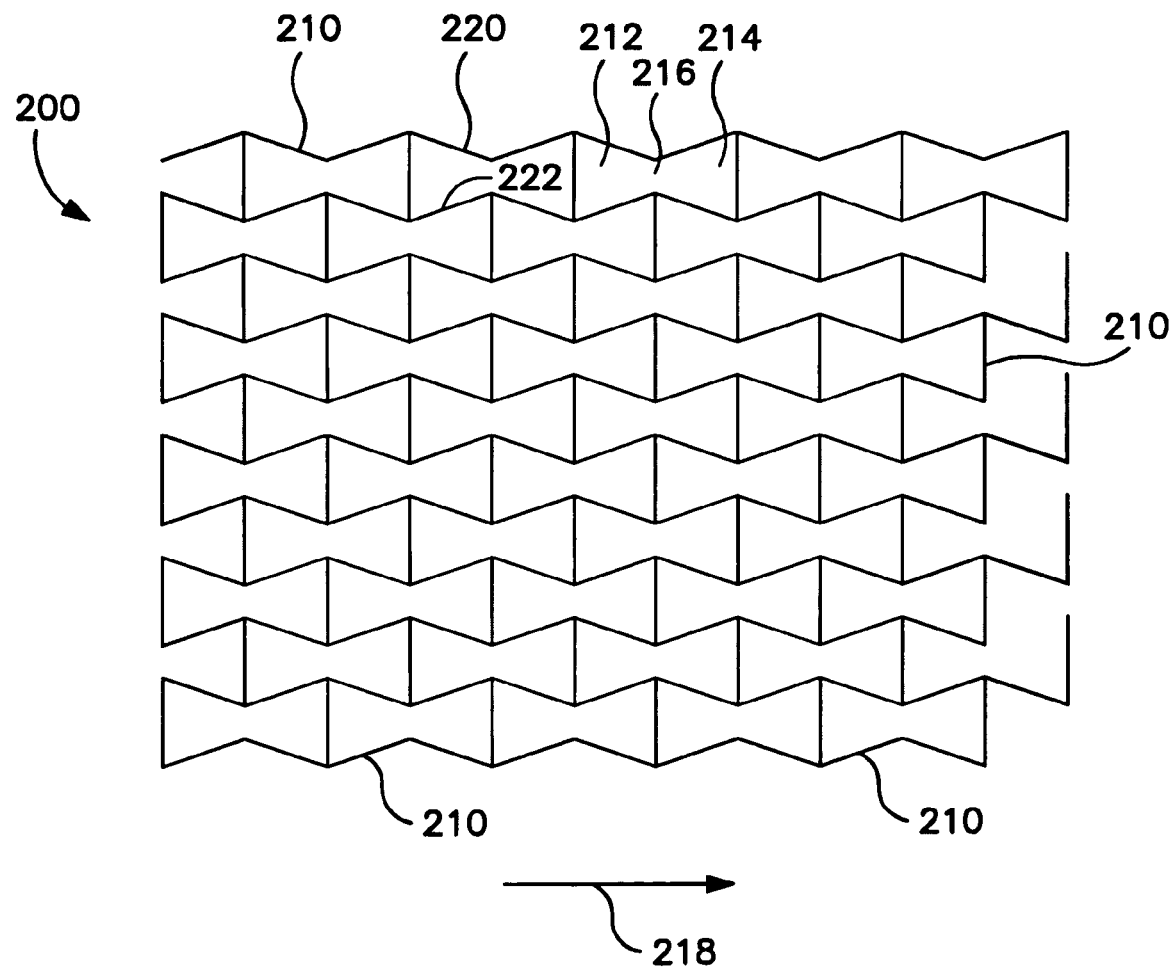
FIG. 5 is a plan view of one embodiment of a bonding pattern made in accordance with the present invention.

For example, referring to FIG. 5, one embodiment of a pattern 200 in accordance with the present invention is shown. As illustrated, the pattern 200 includes a plurality of individual cells 210. Each cell 210 includes expanded regions 212 and 214 and a constricted region 216. The constricted region 216 is positioned in between the expanded regions 212 and 214. When a tissue web containing the bonding pattern 200 as shown in FIG. 5 is pulled in the machine direction as indicated by arrow 218, the constricted regions 216 of the individual cells 210 have a tendency to expand thus lowering the Poisson ratio. More specifically, each cell 210 includes a pair of ribs 220 and 222 which have a tendency to move in an outward direction from each cell when the tissue web is placed under a strain.

Figure 6:
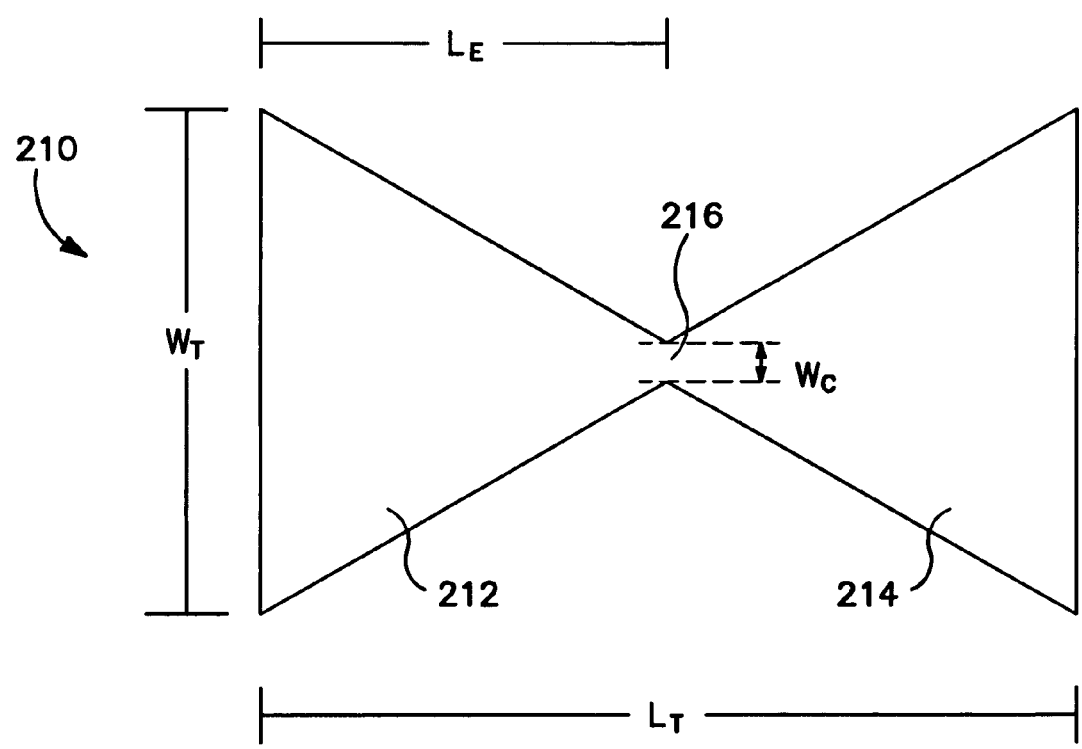
FIG. 6 is a plan view of one embodiment of an enlarged cell that may be contained in a bonding pattern made in accordance with the present invention.

Referring to FIG. 6, an individual cell 210 from the pattern shown in FIG. 5 is illustrated. As shown, the cell 210 includes a total length $L_T$, a total width $W_T$, an expanded region length $L_E$, and a constricted region width $W_C$. For many applications, the total length $L_T$ is at least about twice the total width $W_T$ of each cell.

The width $W_C$ of the constricted area may vary depending upon various factors. In general, the width of the constricted area is less than about 2 mm, such as less than about 1.5 mm, such as from about 0.3 mm to about 1 mm. In one particular embodiment, for instance, the width of the constricted area may be from about 0.4 mm to about 0.8 mm. In one embodiment, the width of the constricted region 216 may be no less than the average length of the fibers used to form the nonwoven material, such as the tissue web.

In an alternative embodiment, however, the constricted region may be no greater than the average length of the fibers in the web. By having the width of the constricted region less than the average length of the fibers used to form the web, strength in the cross direction may be maximized. In fact, the material may exhibit a secondary yield point when stretched in the cross direction.

The expanded regions 212 and 214 of each cell 210 may come in a variety of shapes. The expanded regions, for instance, may have a square, curvilinear, hexagonal, or elliptical shape. In FIG. 5, the expanded regions 212 and 214 have a triangular shape.

The patterns of the present invention may also be interconnected. By interconnected is meant that each cell 210 may share a common border with an adjacent cell. For example, in one embodiment, at least two sides of each cell may be interconnected with adjacent cells. In FIG. 5, for instance, every side of the cells 210 are interconnected with adjacent cells. As shown, FIG. 5 comprises a plurality of rows of cells. The cells in adjacent rows are in a staggered or alternating configuration allowing the cells to be interlocked together.

Figure 7:
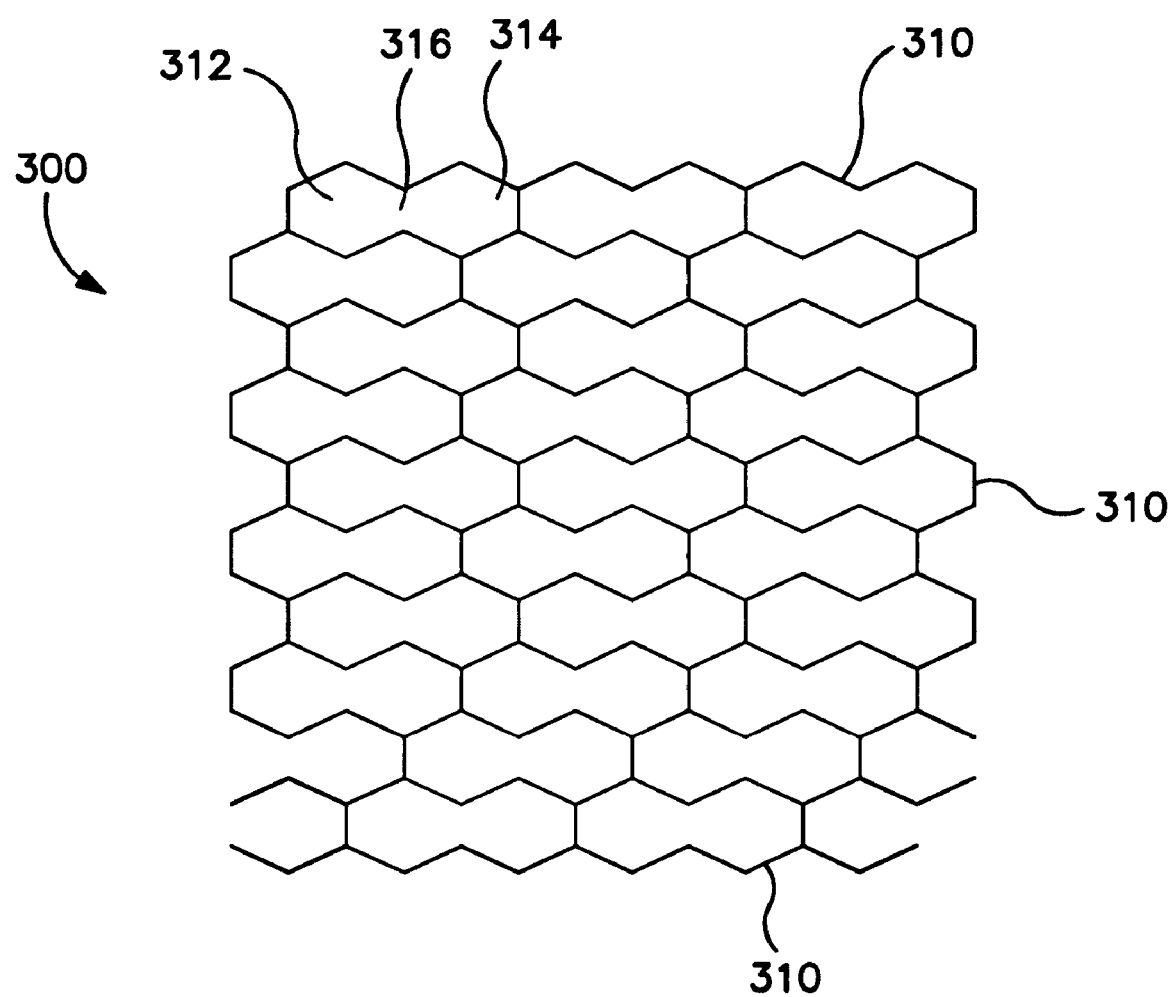
FIG. 7 is a plan view of another embodiment of a bonding pattern in accordance with the present invention.

Referring to FIG. 7, another embodiment of a pattern 300 in accordance with the present invention is shown. As illustrated, the pattern 300 is comprised of individual cells 310. Each cell 310 includes a pair of expanded regions 312 and 314 separated by a constricted region 316. In this embodiment, the expanded regions 312 and 314 have a hexagon-like shape. The cells are also shown in an interconnected arrangement.

Figure 8:
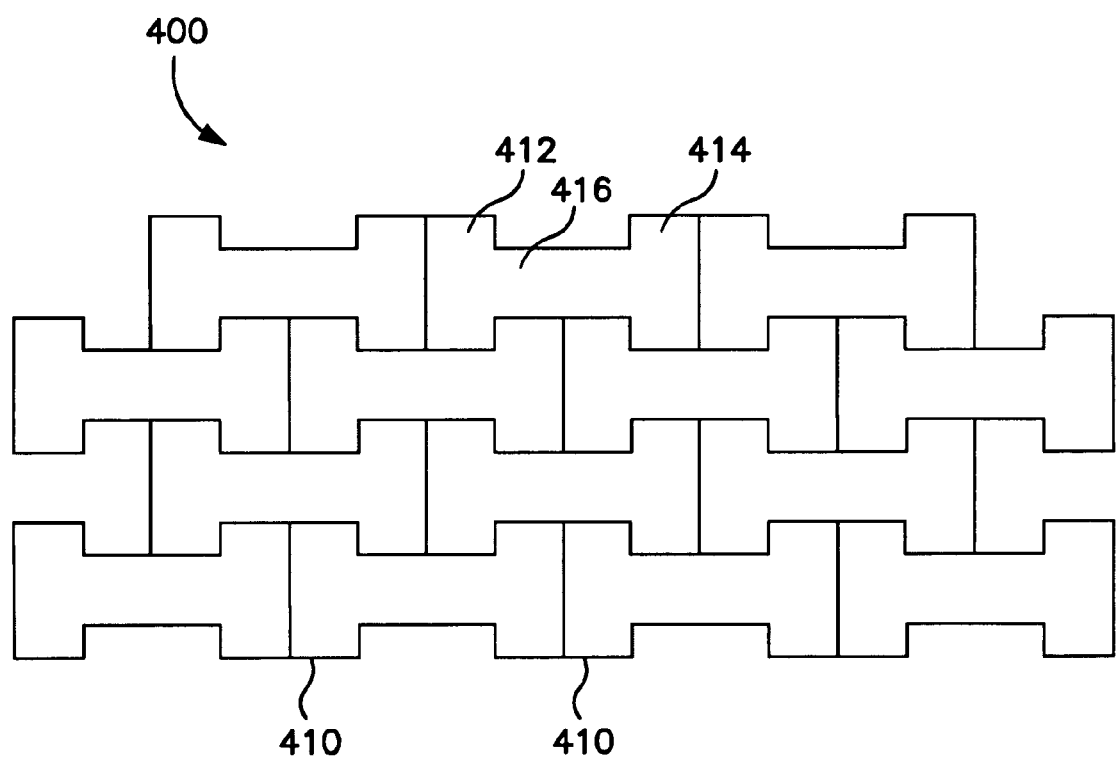
FIG. 8 is a plan view of still another embodiment of a bonding pattern in accordance with the present invention.

Referring to FIG. 8, still another embodiment of a bonding pattern made in accordance with the present invention is shown. In this embodiment, the bonding pattern 400 includes individual cells 410 comprised of a pair of expanded regions 412 and 414 separated by a constricted region 416. In this embodiment, the expanded regions 412 and 414 are in the shape of a rectangle. Again, the cells 410 are in an interconnected and alternating arrangement.

Figure 9:
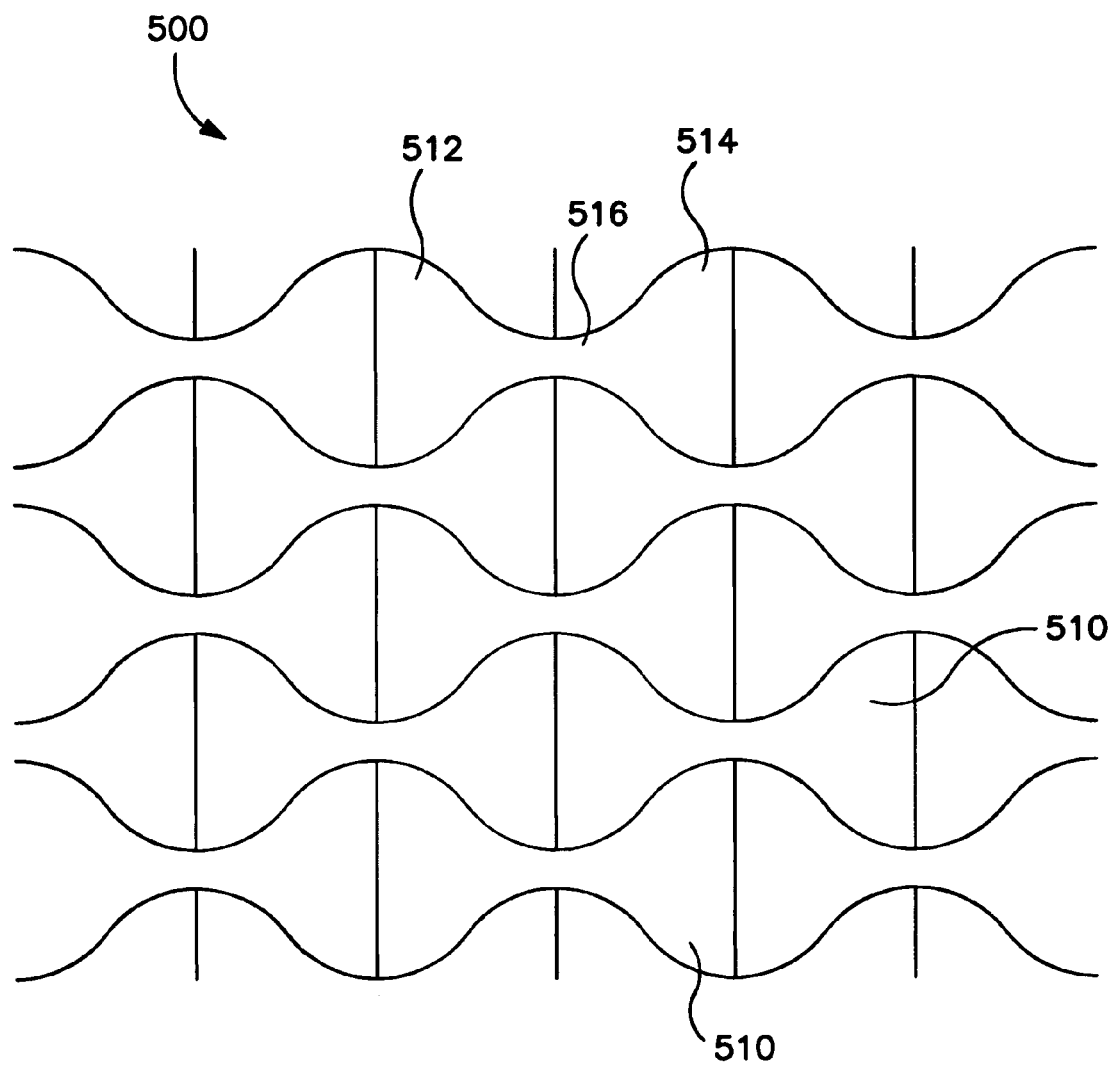
FIG. 9 is a plan view of another embodiment of a bonding pattern in accordance with the present invention.
Figure 10:
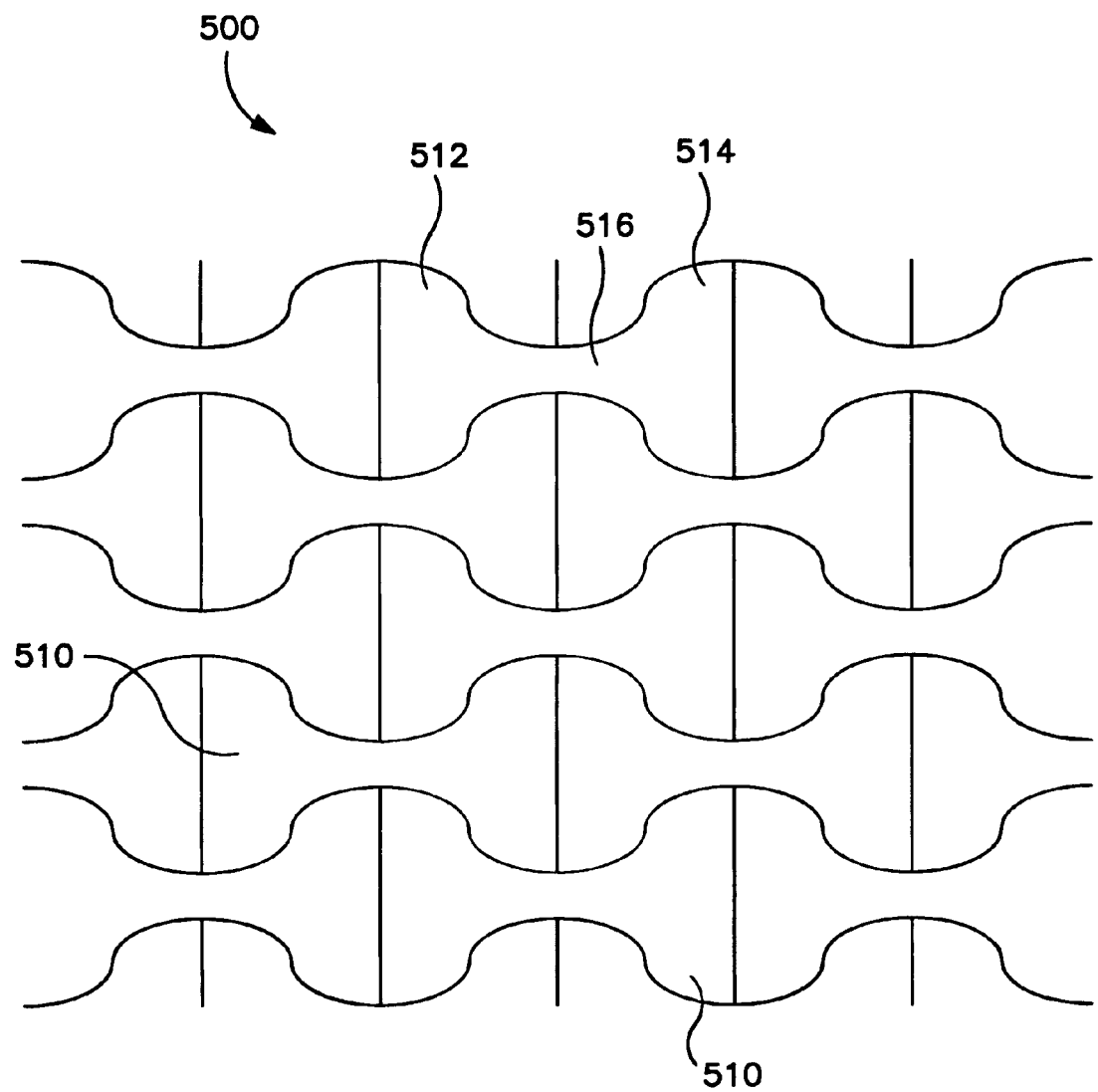
FIG. 10 is a plan view of still another embodiment of a bonding pattern in accordance with the present invention.

In FIGS. 9 and 10, alternative embodiments of bonding patterns generally 500 made in accordance with the present invention are shown. As illustrated, each bonding pattern 500 includes individual cells 510 comprised of expanded regions 512 and 514 separated by constricted regions 516. In this embodiment, the expanded regions have a curvilinear shape.

Figure 11:
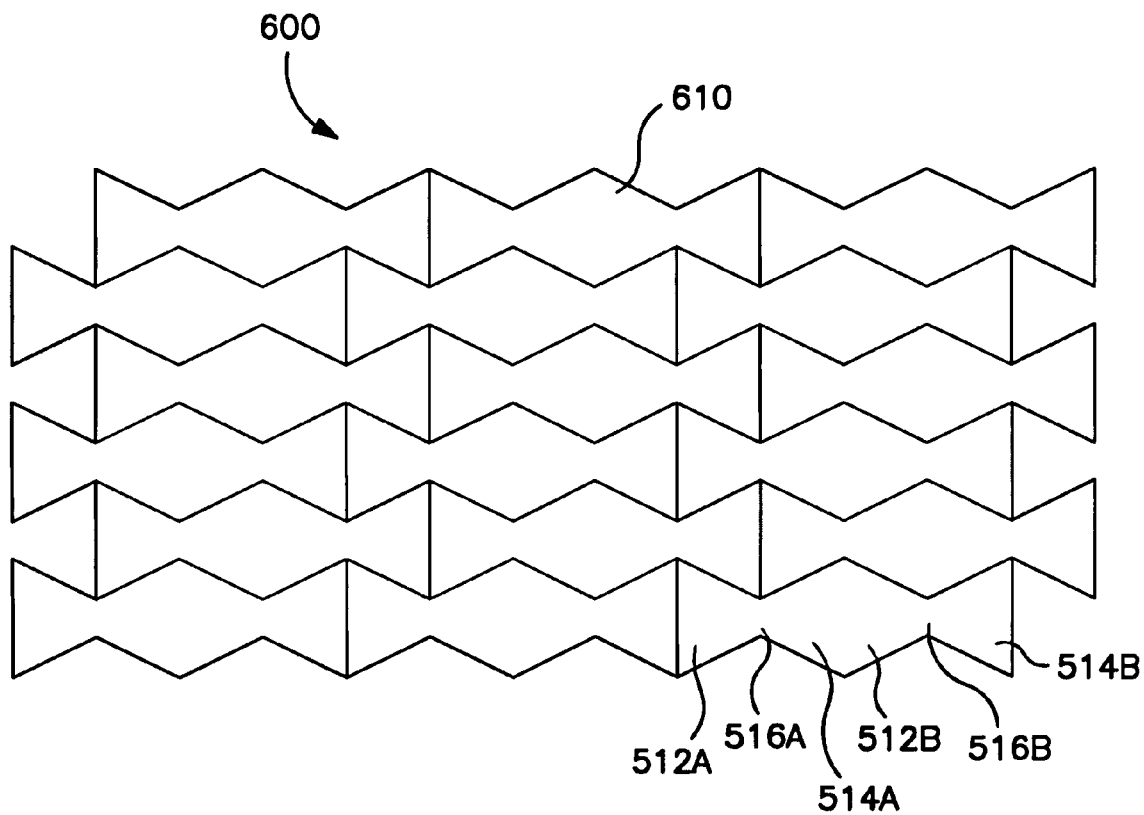
FIG. 11 is a plan view of another embodiment of a bonding pattern in accordance with the present invention.

Referring to FIG. 11, still another embodiment of a bonding pattern generally 600 made in accordance with the present invention is shown. The bonding pattern shown in FIG. 11 is somewhat similar to the bonding pattern shown in FIG. 5. In FIG. 11, the individual cells 610 include two constricted regions 516A and 516B. The constricted regions 516A and 516B are surrounded by expanded regions. For instance, constricted region 516A may be considered to be bordered by expanded regions 512A and 514A, while constricted region 516B may be considered to be bordered by expanded region 512B and 514B. As shown, expanded region 514A and expanded region 512B may also be considered to form a single expanded region.

According to the present invention, the bonding materials are applied to each side of the tissue web so as to cover from about 5% to about 90% of the surface area of the web, such as from about 30% to about 80% of the surface area of the web. In general, the amount of surface area covered by the bonding material is determined by the particular pattern used, the size of the individual cells, and the width of the bond lines. In many applications, the bonding material may cover from about 40% to about 60% of the surface area of each side of the web. The total amount of bonding material applied to each side of the web can be in the range of from about 2% to about 20% by weight, based upon the total weight of the web, such as from about 4% to about 10% by weight.

At the above amounts, the bonding materials can penetrate the tissue web from about 10% to about 70% of the total thickness of the web. In most applications, the bonding materials should at least penetrate from about 10% to about 15% of the thickness of the web.

Once a bonding material is applied to each side of the tissue web as shown in FIG. 3, the Poisson ratio of the tissue web is substantially reduced when the web is stressed in the machine direction. The amount the Poisson ratio is reduced may depend on various factors. For instance, the degree to which the Poisson ratio is reduced may depend upon the actual pattern selected, the size of the individual cells contained in the pattern including the size of the constricted region, the basis weight of the tissue web, besides various other factors. In some embodiments, it is believed that a tissue web may be produced actually having a negative Poisson ratio such that the width of the web does not shrink and may even expand when the web is pulled in the lengthwise direction.

To achieve a negative Poisson ratio, it is believed that in addition to the particular pattern chosen, the basis weight of the tissue web and the amount the fibers have been debonded within the tissue web may play an important role. For instance, it is believed that the lowest Poisson ratios are achieved when treating a tissue web that has been highly debonded and that has a basis weight of less than about 45 gsm, such as less than about 40 gsm, such as less than about 35 gsm, such as less than about 30 gsm.

In other embodiments, it may not be desirable or necessary to produce a tissue web having a negative Poisson ratio in order to receive various benefits and advantages. For instance, in other embodiments, the Poisson ratio may be reduced by greater than about 30%, such as greater than about 40%, or such as greater than about 50% when the bonding materials are applied. For instance, the Poisson ratio of the tissue web may be less than about 0.3, such as less than about 0.2, such as less than about 0.1.

In addition to significantly decreasing the Poisson ratio of tissue webs, the process of the present invention may also be used to increase total energy absorption and increase cross-direction stretch.

According to the process of the current invention, numerous and different paper products can be formed. For instance, the paper products may be single-ply wiper products. The products can be, for instance, facial tissues, bath tissues, paper towels, napkins, industrial wipers, and the like.

In an alternative embodiment, tissue webs made according to the present invention can be incorporated into multiple ply products. For instance, in one embodiment, a tissue web made according to the present invention can be attached to one or more other tissue webs for forming a wiping product having desired characteristics. The other webs laminated to the tissue web of the present invention can be, for instance, a wet-creped web, a calendered web, an embossed web, a through-air dried web, a creped through-air dried web, an uncreped through-air dried web, an airlaid web, and the like.

In one embodiment, when incorporating a tissue web made according to the present invention into a multiple ply product, it may be desirable to only apply a bonding material to one side of the tissue web and to thereafter crepe the treated side of the web. The creped side of the web may then be used to form an exterior surface of a multiple ply product. The untreated and uncreped side of the web, on the other hand, may be attached by any suitable means to one or more plies.

Figure 4:
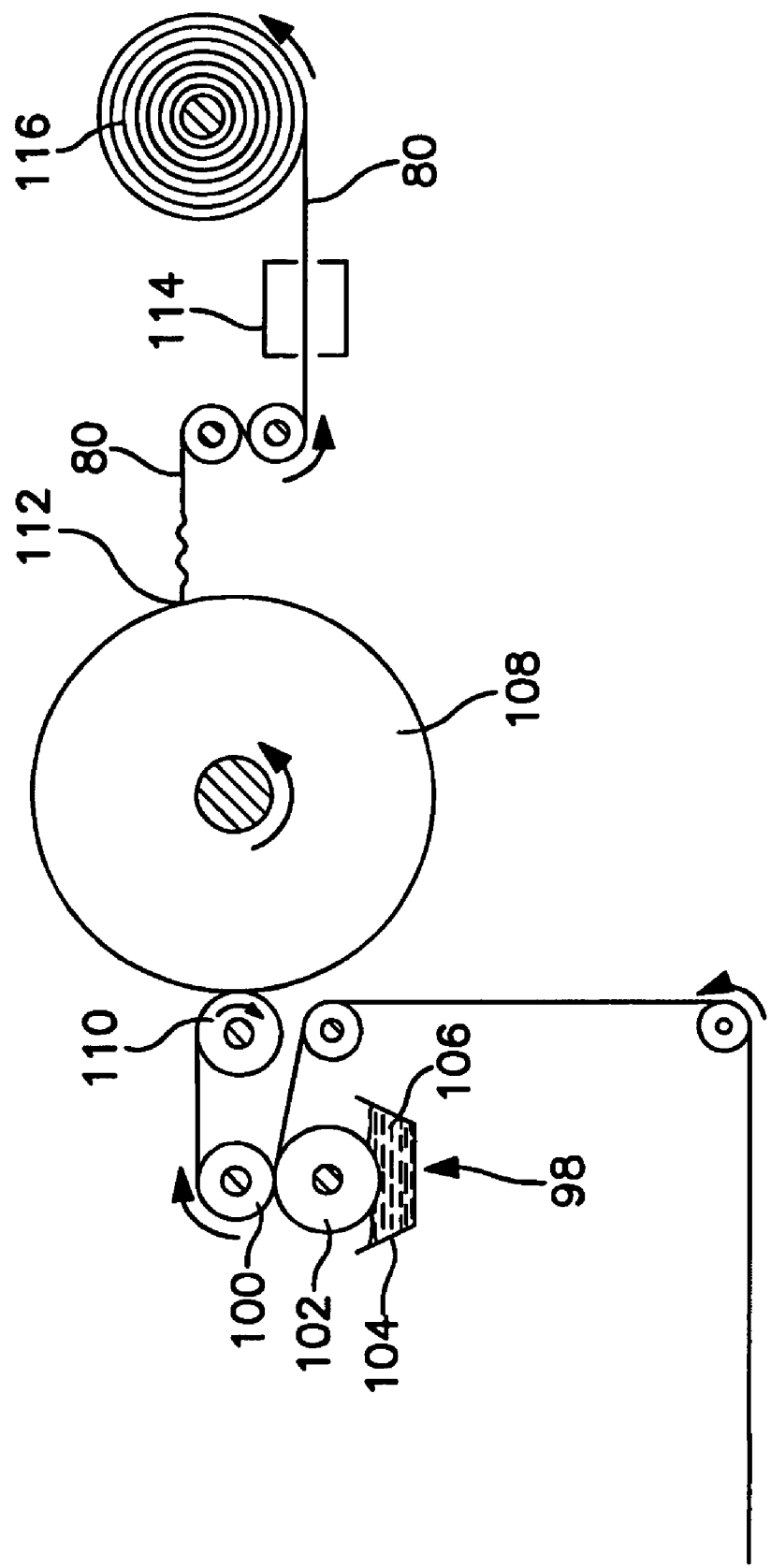
FIG. 4 is a schematic diagram of an alternative embodiment of a process for applying a bonding material to one side of a tissue web and creping one side of the web in accordance with the present invention.

For example, referring to FIG. 4, one embodiment of a process for applying a bonding material to only one side of a tissue web in accordance with the present invention is shown. The process illustrated in FIG. 4 is similar to the process shown in FIG. 3. In this regard, like reference numerals have been used to indicate similar elements.

As shown, a web 80 is advanced to a bonding material application station generally 98. Station 98 includes a transfer roll 100 in contact with a rotogravure roll 102, which is in communication with a reservoir 104 containing a bonding material 106. At station 98, the bonding material 106 is applied to one side of the web 80 in a preselected pattern, such as those shown in FIGS. 5, 7, 8, 9,10 or 11.

Once the bonding material is applied, web 80 is adhered to a creping roll 108 by a press roll 110. Web 80 is carried on the surface of the creping drum 108 for a distance and then removed therefrom by the action of a creping blade 112. The creping blade 112 performs a controlled pattern creping operation on the treated side of the web.

From the creping drum 108, the tissue web 80 is fed through a drying station 114 which dries and/or cures the bonding material 106. The web 80 is then wound into a roll 116 for use in forming multiple ply products.

In addition to print creping processes, it should be understood that the patterns of the present invention may be incorporated into tissue webs using other methods. Further, it should also be understood that the patterns of the present invention may be incorporated into other nonwoven materials.

For instance, the nonwoven materials may comprise in addition to tissue webs, meltspun webs such as meltblown webs and spunbond webs, bonded carded webs, hydroentangled webs, and the like. The nonwoven webs may also be elastic and may contain, for instance, an elastomeric material.

The manner in which the pattern is incorporated into the nonwoven materials may vary depending upon the particular circumstances. For instance, the pattern may be incorporated into the web by topically applying a bonding material to one or both sides of the web such as shown in FIG. 3 but without creping. Alternatively, the web may be formed on a 3-dimensional topographical forming surface. The forming surface may have a pattern of the present invention incorporated into it which is transferred to the web upon formation. For instance, the pattern may be incorporated into a tissue web during a throughdrying process. In one particular embodiment, once the pattern is incorporated into the web, the raised portions of the pattern may be printed with a bonding material. After being printed with a bonding material, the web may be pressed against a creping drum and creped from the drum.

The pattern may also be incorporated into the web through thermal bonding. For instance, the web may be a meltblown web, a spunbond web, a bonded carded web, a coform web, a tissue web, or a hydroentangled web containing, for instance, synthetic fibers. In this embodiment, the web may be fed through a nip being formed from a heated embossing roll which embosses the pattern into the web.

As used herein, a "meltblown web" refers to a web made from fibers formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin. et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbond web" refers to a web made from small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers can sometimes have diameters less than about 40 microns, and are often between about 5 to about 20 microns.

As described above, the wiper may also be formed from a hydroentangled nonwoven fabric. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled nonwoven fabrics of staple length fibers and continuous filaments are disclosed, for example, in U.S. Pat. No. 3,494,821 to Evans and U.S. Pat. No. 4,144,370 to Bouolton, which are incorporated herein in their entirety by reference thereto for all purposes. Hydroentangled composite nonwoven fabrics of a continuous filament nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes.

The wiper may also be formed from a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

The pattern of the present invention may be incorporated into the above nonwoven materials containing thermoplastic fibers using methods known in the art. For instance, bonding techniques for thermally bonding webs or adhesively bonding webs are disclosed in U.S. Pat. No. 3,855,046, U.S. Pat. No. 5,620,779, U.S. Pat. No. 5,962,112, U.S. Pat. No. 6,093,665, U.S. Pat. No. 5,284,703, U.S. Pat. No. 6,103,061, and U.S. Pat. No. 6,197,404, which are all incorporated herein by reference.

Once the pattern is incorporated into a nonwoven material, various benefits and advantages are realized. For instance, by reducing the Poisson ratio of the material, the material may be more easily processed. Specifically, since the pattern counteracts the natural tendency of the material to shrink while being pulled, processing equipment does not have to compensate for width loss. Thus, the material may be easier to form, to combine with other materials, and/or to form into a product.

In some applications, incorporating a pattern according to the present invention into a nonwoven material also increases the cross-machine direction stretch characteristics of the material. In fact, in some embodiments, the cross direction stretch characteristics will increase approximately to that of the machine direction stretch characteristics. The pattern has also been found to improve the drape of some materials and to improve tear resistance in the cross-machine direction. When applying the pattern using a latex, latex consumption may also be reduced in comparison to other patterns used in the past. The pattern may also further increase total energy absorption (TEA) when the material is stressed.

In some applications, incorporating a pattern according to the present invention into a nonwoven web may actually serve to increase process capacity. For example, in some embodiments, nonwoven materials are formed that have a width of about 100 inches. The 100-inch parent rolls are then converted into individual rolls having a width of approximately 11 inches. In the past, however, during converting operations the web has a tendency to shrink in width such that a 100-inch parent roll may only produce eight product rolls or less. By controlling shrinkage in the width direction according to the present invention, however, it is possible to produce nine product rolls from a parent roll that is 100 inches wide. In particular, shrinkage can be controlled to be less than 1.5%, such as less than 1% during the process. In this manner, capacity of the process is increased.

Nonwoven materials made in accordance with the present invention may be used in single ply applications or may be combined with other plies to form laminates. Laminates made according to the present invention can be made by any suitable technique or process.

In one embodiment, for instance, a nonwoven web may be molded with an impression device in order to form a raised auxetic pattern in accordance with the present invention. A bonding material may then be printed onto the raised portions of the pattern and the web may then be adhered to another web for forming a laminate. In this embodiment, the raised pattern may be created into the web during formation of the web using a 3-dimensional forming fabric or may be embossed into the web. In one particular embodiment, a first web with a first raised auxetic pattern may be bonded to a second web with a second raised auxetic pattern, wherein the second raised pattern is a mirror image of the first raised auxetic pattern. When joining the webs together, the patterns may be registered together.

As stated above, nonwoven webs, such as tissue webs containing a pattern according to the present invention have a relatively low Poisson ratio in the cross-machine direction when stressed in the machine direction. The actual resulting Poisson ratio of the material depends on various factors including the mariner in which the pattern is incorporated into the web and the material used to form the web. In many applications, for instance, the Poisson ratio of the web may be less than about 0.3, such as less than about 0.25, such as less than about 0.2, or such as less than about 0.15. For instance, in one embodiment, the Poisson ratio of the resulting material may be less than 0.1. Further, it is believed that in some embodiments, the Poisson ratio may even be negative meaning that the material actually increases in width when pulled in the lengthwise direction.

The present invention may be better understood with reference to the following examples.

EXAMPLE 1

Computer modeling of different print-creped tissue products was completed to demonstrate the ability of the present invention to significantly lower Poisson ratios.

Specifically, two bonding patterns made in accordance with the present invention were compared with a control. The first bonding pattern was similar to the one shown in FIG. 5 wherein the expanded regions had a triangular shape. The second bonding pattern was similar to the bonding pattern illustrated in FIG. 7, wherein the expanded regions were shaped like hexagons. The control was a bonding pattern as shown in FIG. 7 except all sides of the hexagons were enclosed. The pattern thus appeared to be honeycomb-like. Each hexagon had a length of 3 mm and a width of 3 mm.

During computer simulations, the computer was programmed to predict transverse (cross direction) strain versus longitudinal (machine direction) strain for a print-creped, print-creped web containing the patterns on each side of the web.

Figure 15:
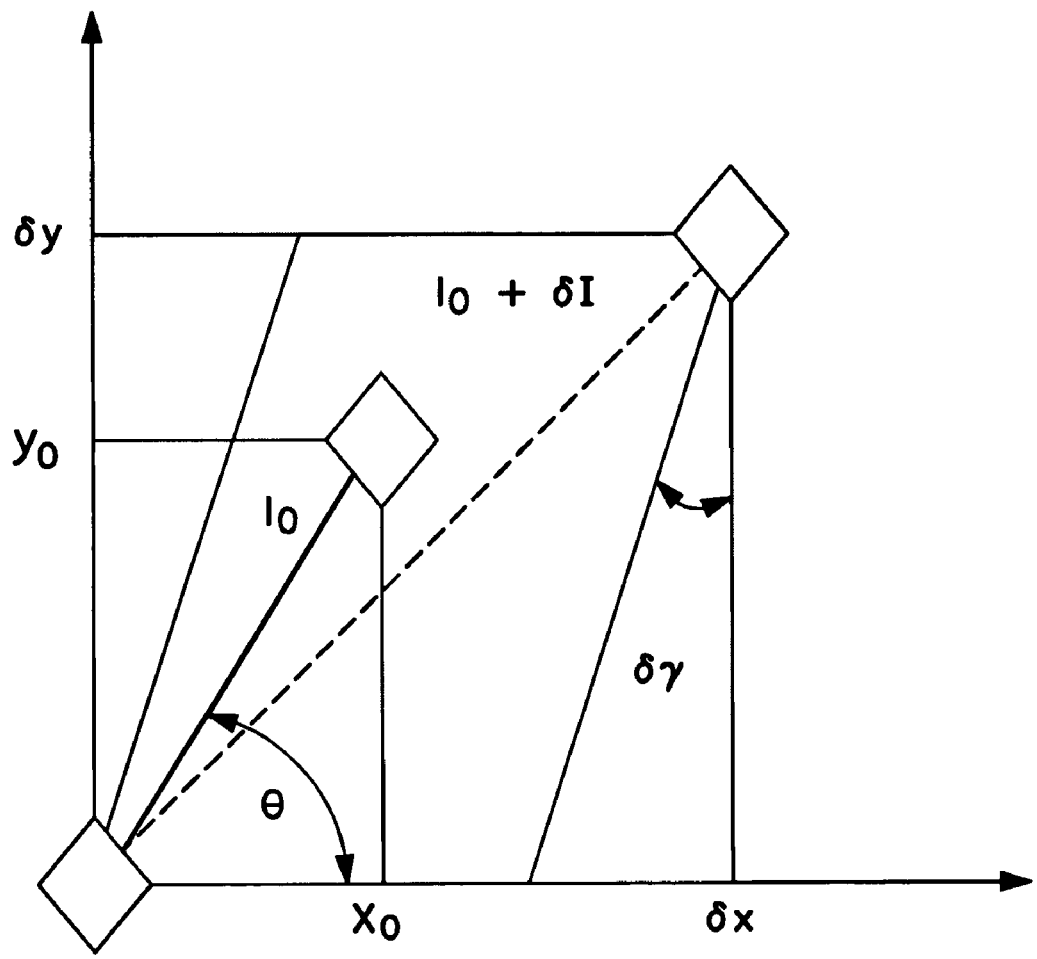
FIG. 15 is a graphical depiction of an incremental deformation of a fiber segment in a web.

The computer model was based on the incremental deformation principle. Referring to FIG. 15, a fiber segment of original length $l_0$, oriented at an angle $\theta$ relative to the machine direction (MD) is graphically depicted. Both ends of this fiber segment are anchored at two different bond sites, shown as diamonds on FIG. 15. As the web is deformed, the fiber segment is extended to a length $(l_0+\delta l)$ such that:

$$(l_0+\Delta l)^2 = (y_0+\Delta y)^2 + (x_0+\Delta x + \tan \delta\gamma \cdot ((y_0+\Delta y)))^2$$

where $\Delta l$ is the elongation of the fiber $\Delta x$ is the elongation component in the machine direction $\Delta y$ is the elongation component in the cross direction, and $\delta\gamma$ is the shear strain of the web.

In the case of very small increments of strain at each deformation step, the incremental strain, $\delta\epsilon_\theta$, and the incremental specific stress, $\Delta f_\theta$, in the bridging fiber are respectively, $$\delta\epsilon_\theta = (l_x/l_0)\delta\epsilon_x \cos\theta + (l_y/l_0)\delta\epsilon_y \sin\theta + \delta\gamma\sin\theta\cos\theta$$

and $$\Delta f_\theta = E(\epsilon)[(l_x/l_0)\delta\epsilon_x \cos\theta + (l_y/l_0)\delta\epsilon_y \sin\theta + \delta\gamma \sin\theta \cos\theta]$$

The global coordinates system (MD and CD direction) were obtained from the local coordinate system (fiber direction) by the rotation angle of $\theta$ at which the fiber is oriented. As the model employed the input generated from the image simulation, the contribution of all fibers to the global coordinates could be obtained by simply summing the contributions of each fiber without the need for considering specific structural parameters of the web such as the web areal density and fiber linear density.

The incremental forces $\Delta F_x$ and $\Delta F_y$ in MD and CD, respectively, and the incremental shear force $\Delta F_{xy}$ acting on the circumscribed rectangle are given in the matrix form as:

$$\begin{Bmatrix} \Delta F_x \\ \Delta F_y \\ \Delta F_{xy} \end{Bmatrix} = \begin{pmatrix} Q_{11} & Q_{12} & Q_{13} \\ Q_{21} & Q_{22} & Q_{23} \\ Q_{31} & Q_{32} & Q_{33} \end{pmatrix} \cdot \begin{Bmatrix} \delta\epsilon_x \\ \delta\epsilon_y \\ \delta\epsilon_{xy} \end{Bmatrix}$$

where:

$$Q_{11} = \sum_{n=1}^{N} E(\epsilon_n)\cos^3\theta_n (l_{nx}/l_{n0})$$

$$Q_{12} = \sum_{n=1}^{N} E(\epsilon_n)\sin\theta_n\cos^2\theta_n (l_{ny}/l_{n0})$$

$$Q_{13} = \sum_{n=1}^{N} E(\epsilon_n)\sin\theta_n\cos^3\theta_n$$

$$Q_{21} = \sum_{n=1}^{N} E(\epsilon_n)\sin^2\theta_n\cos\theta_n (l_{nx}/l_{n0})$$

$$Q_{22} = \sum_{n=1}^{N} E(\epsilon_n)\sin^3\theta_n (l_{ny}/l_{n0})$$

$$Q_{23} = \sum_{n=1}^{N} E(\epsilon_n)\sin^3\theta_n\cos\theta_n$$

$$Q_{31} = \sum_{n=1}^{N} E(\epsilon_n)\sin\theta_n\cos^2\theta_n (l_{nx}/l_{n0})$$

$$Q_{32} = \sum_{n=1}^{N} E(\epsilon_n)\sin^2\theta_n\cos\theta_n (l_{ny}/l_{n0})$$

$$Q_{33} = \sum_{n=1}^{N} E(\epsilon_n)\sin^2\theta_n\cos^2\theta_n$$

where, $l_x$ is the relative distance between the two bond sites in the global MD, $l_y$ is the relative distance between the two bond sites in the global CD, $E(\epsilon_n)$ is the local modulus of the nth fiber, obtained from the load-strain curve of the fiber (in general, $E(\epsilon_n)$ varies with extension if the fiber load-extension behavior is nonlinear), $\delta\epsilon_x$ is the incremental tensile strain of the web in MD, $\delta\epsilon_y$ is the incremental tensile strain of the web in CD, and $\delta\gamma$ is the shear strain of the web.

Assuming a rectangular area circumscribing the bond site, oriented parallel to the MD and CD, the incremental linear tensile forces and shear forces were defined as the forces acting on the unit width and height of the rectangular region.

The program modeled the stress/strain behavior by incrementally straining the fabric and computing the linear stress components at each strain level. The program calculated the fiber strain from the original fiber length and the elongated fiber length. To form the global constitution equation, the fiber strain component was transformed at the global x-y coordinate using the delta(x), delta(y), shear angle, and their original values. At each incremental strain level, the resulting force components were determined. The model was programmed such to ensure that the force balance was maintained. That is, the summation of all force components must equal zero. If the force balance was not maintained, the force brought about by the changes in strain was re-calculated until convergence was achieved. Once convergence was met, the total force was checked against the amount of force required to fail the fibers. The bonding strength was assumed to exceed the rupture strength of the fibers. If the force required to fail the fibers in the computational model were higher than the corresponding experimental data, those elements were eliminated and the force balance convergence was reevaluated. If the model met web failure condition, the resulting data was automatically saved and displayed for review.

The simulation parameters were based on pulp fiber dimensions of 2.5 mm by 20 microns and a basis weight range of 10 to 30 gsm. The incremental strain parameter was set at 0.01, and the debonding force was assumed to be 0.05 N. The CD strain interval was 0.02.

Figure 12:
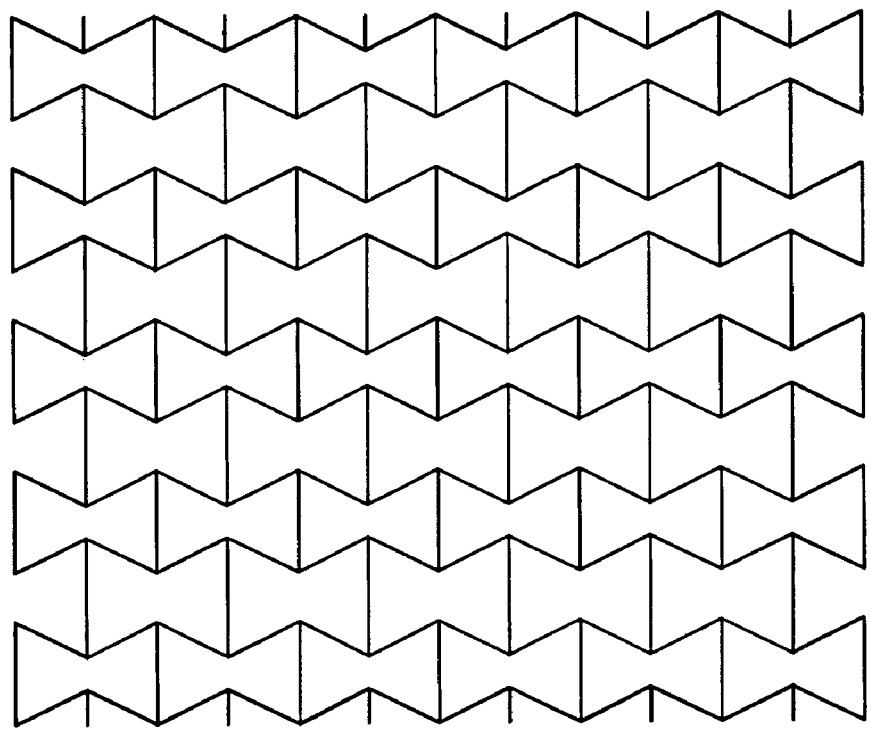
FIGS. 12 through 14 are the graphical results obtained in Example 1 below.
Figure 12:
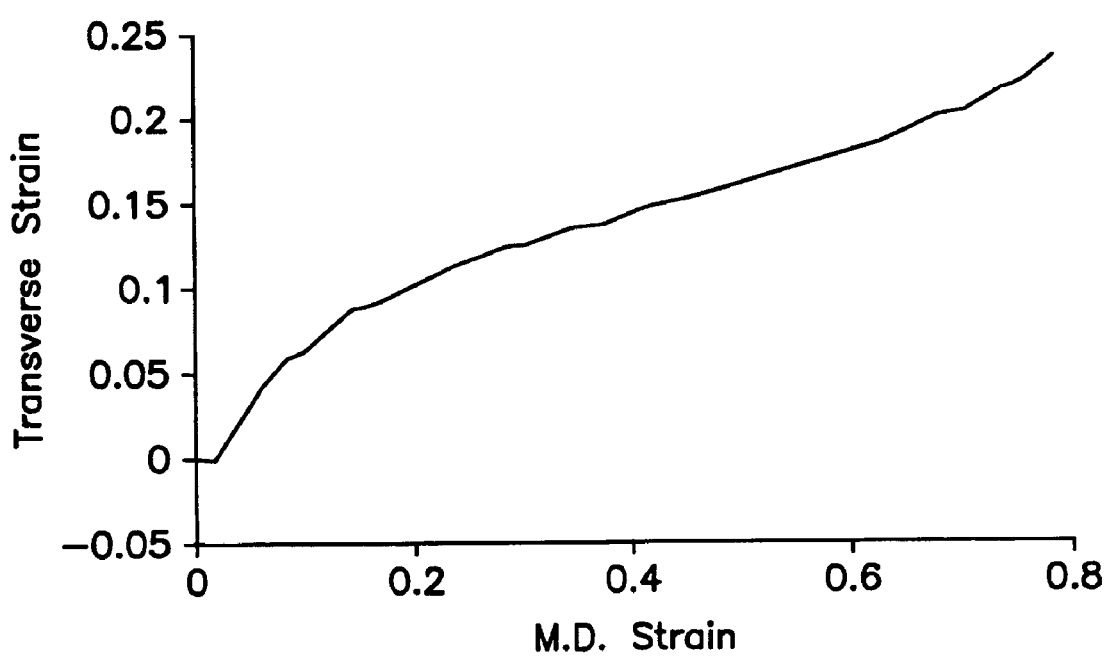
Figure 13:
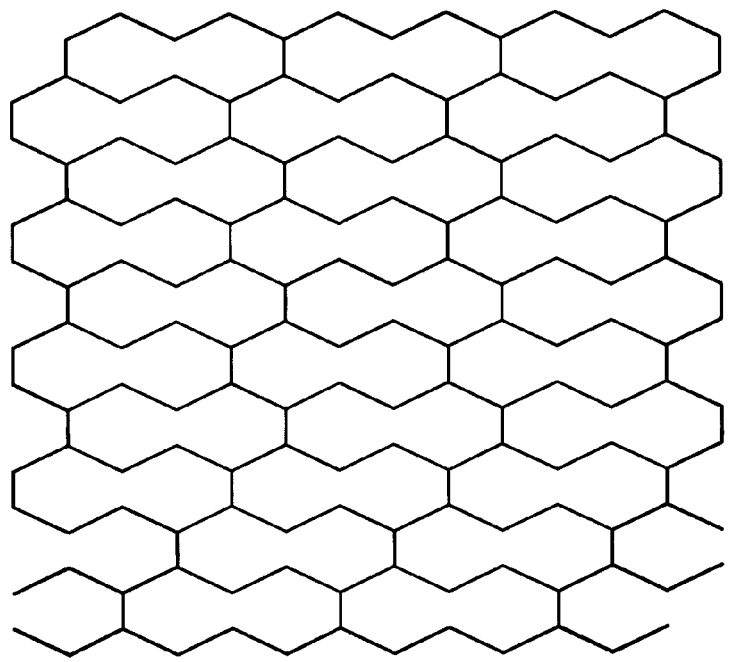
Figure 13:
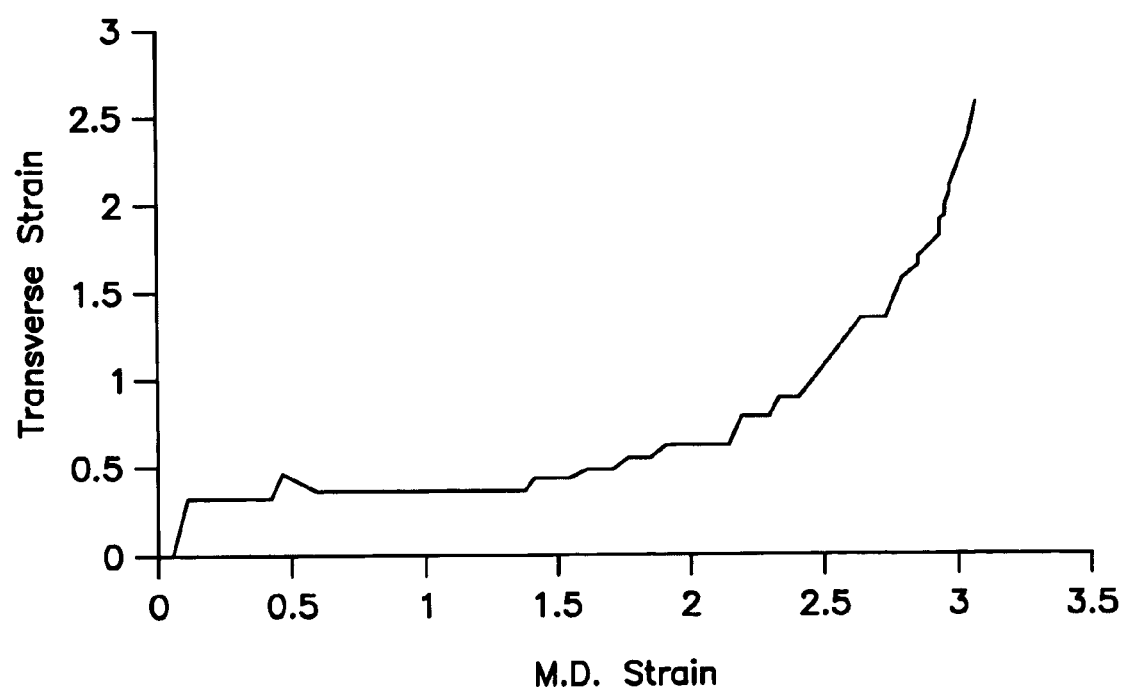
Figure 14:
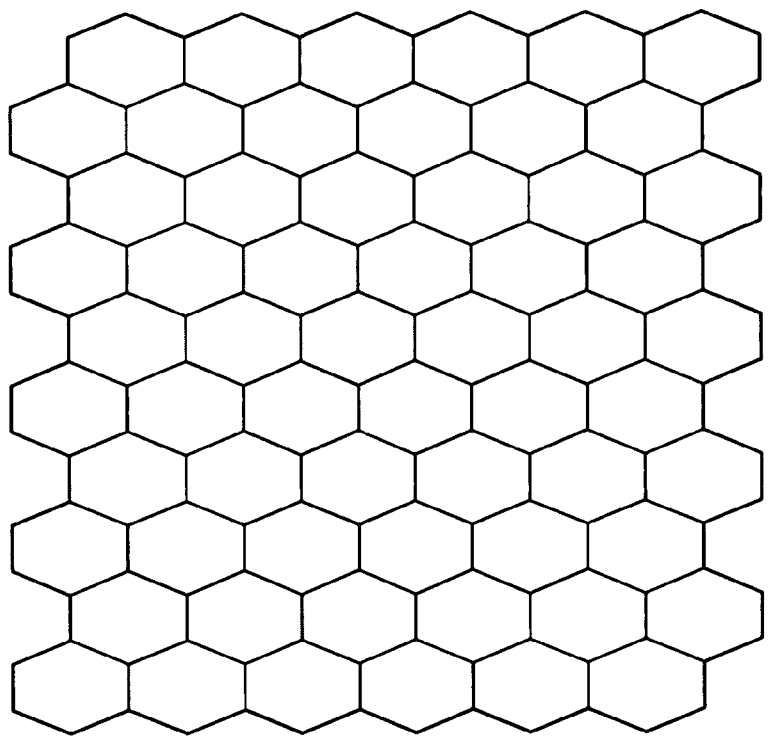
Figure 14:
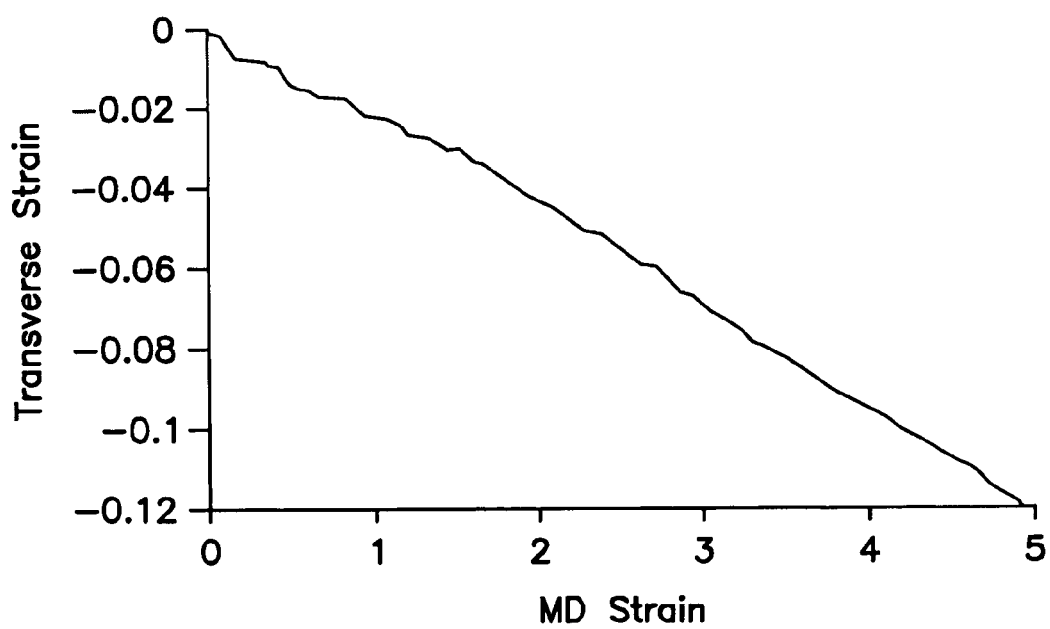

The results are shown in FIGS. 12-14. In particular, FIG. 12 is the strain versus strain curve for the first pattern according to the present invention similar to the one shown in FIG. 5, FIG. 13 is the strain versus strain curve for the second pattern according to the present invention as shown in FIG. 7, while FIG. 14 is the strain versus strain curve for the control in which the pattern was comprised of enclosed hexagons. As shown, the slope of the graph for the two tissue products made according to the present invention is opposite to the slope of the graph for the control. Thus, tissue webs made according to the present invention exhibited a negative Poisson ratio.

EXAMPLE 2

In order to demonstrate that the bonding patterns of the present invention are capable of significantly reducing the Poisson ratio of a tissue web, an uncreped through-air dried (UCTAD) base web was treated with a bonding material according to the teachings of the present invention and the web was then subjected to various standardized tests. During this example, the tissue webs were treated with a bonding material in accordance with the present invention but were not creped from a creping surface. Further, none of the products were optimized in the example. This example was completed merely to show that applying a bonding material to a tissue web according to an auxetic pattern will significantly lower Poisson ratios.

The UCTAD based web was formed in a process similar to the method shown in FIG. 1. In this particular example, the base web was made from a stratified fiber furnish containing a center layer of fibers positioned between two outer layers of fibers. Both outer layers of the UCTAD base web contained 100% LL19, a northern softwood Kraft pulp and up to 6 kg/MT of TQ1003 debonder obtained from the Hercules Corporation. The center layer contained 50% BCTMP pulp obtained from Miller Western Pulp Ltd. and 50% of the aforementioned softwood Kraft pulp with up to 6 kg/MT of TQ1003 debonder.

This example had 3 separate runs, each with a different test material. All three runs used the same basesheet and all bonding material used was from the same batch. The bonding material contained the bonding agent AirFlex 426, a carboxylated vinyl acetate-ethylene terpolymer, obtained from Air Products, Inc. of Allentown, Pa. The bonding agent was mixed with Nalco 7565 defoamer, water, sodium hydroxide, and KYMENE 2064, an epoxy functional polymer.

The bonding material was applied to the basesheet using a flexographic printing procedure in which the pattern was printed on both sides of the sheet. The samples were not creped after the bonding material was applied. For Run 1, a photopolymer plate was used to print a diamond pattern made to match the direct gravure pattern used on Kleenex® Viva® paper towels. For Run 2, the Auxetic pattern shown in FIG. 5 was used instead of the Viva® diamond pattern, and once again, a photopolymer plate was employed for the printing. Run 3 printed the same pattern of Run 2 from FIG. 5, but used a natural rubber plate.

Approximately 15 to 20 feet of material was printed for each run. The samples were placed in the temperature and humidity controlled lab for at least four (4) hours. The lab maintained a constant temperature of 23±2° C. and relative humidity of 50±5%. Machine direction (MD) samples having a width of three inches (3") were then cut out of the center of each sample. Ten (10) samples were prepared for each run and these samples were used for all further testing.

The samples were first used to determine a Poisson Ratio using a simple elongation test. The term "elongation" refers to the increase in length of a sample during testing. To elongate the samples a Synergie Tensile Frame available from MTS Systems, Corp. located in Eden Prairie, Minn., was used. During the test, each end of a sample was placed in an opposing clamp. The clamps held the material in the same plane, and then the clamps were moved apart until the sample had a MD length of 4.5", resulting in an elongation of 0.5". The width in the cross-machine direction (CD) was measured for the sample before and after elongation, and the two values were used to calculate the Poisson Ratio. As defined in the detailed description, the Poisson Ratio is the ratio of the transverse contraction strain to the longitudinal extension strain in the direction of the stretching force. The mathematical expression for the ratio contains a leading negative sign so that normal materials, which decrease in width as they are stretched lengthwise, will have a positive ratio. Therefore, for the current example, the Poisson Ratio was calculated as the negative ratio of the change in width in, the CD direction to the change in length in the MD direction as shown below. The average Poisson Ratio for each of the three runs is given in Table 1 below.

TABLE 1

Poisson Ratio Results $$\text{PoissonRatio} = -\left[\frac{(\text{CDwidth: elongated}) - (\text{CDwidth: relaxed})}{(\text{MDlength: elongated}) - (\text{MDlength: relaxed})}\right]$$

| Run | Pattern | Average Poisson Ratio |
|---|---|---|
| 1 | Diamond | 0.4316 |
| 2 | Auxetic Photopolymer (PP) | 0.2316 |
| 3 | Auxetic Natural Rubber NR | 0.2316 |

The samples were then subjected to standardized tests for tensile strength and stretch. The tensile strength and the percent stretch of samples were determined in both the machine direction and in the cross-machine direction. The results are expressed in grams to break per mm width of at rest sample (in the stretched dimension) and percent stretch before breakage.

Once again a Synergie Tensile Frame was used to elongate the samples in order to determine the tensile strengths. The samples were once again placed in opposing clamps and then the clamps were moved apart at a constant rate. The clamps moved apart until breakage occurred in order to measure the tensile strength. Percent elongation was calculated as the positive change in the length of the sample divided by the length of the sample at rest. The results of these tests are shown in Table 2 below:

TABLE 2

Tensile Test Results

| Run | Pattern | MD Strength (grams/76 mm) | MD Stretch (%) | CD Strength (grams/76 mm) | CD Stretch (%) |
|---|---|---|---|---|---|
| 1 | Diamond | 2261.7 | 17.14 | 1603.7 | 12.92 |
| 2 | Auxetic PP | 1529.6 | 20.97 | 1054.7 | 10.93 |
| 3 | Auxetic NR | 1680.3 | 21.48 | 1072.6 | 11.07 |

As shown above, simply applying a pattern of the present invention to a tissue web without optimization may significantly decrease the Poisson ratio of the material.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A tissue product comprising:
   a tissue web containing pulp fibers, the tissue web having a first side and a second side, said tissue web defining a width and a lengthwise direction;
   a bonding material applied to the first side of the tissue web in a pattern, the pattern comprising a plurality of individual cells, each cell comprising first and second expanded regions connected together by a constricted region; and
   wherein the first side of the tissue web has been creped after application of the bonding material, and wherein the tissue web has a negative Poisson ratio such that the tissue web increases in width when pulled in the lengthwise direction.

2. A tissue product as defined in claim 1, wherein the individual cells have a total length and a total width, the total length having a distance that is at least twice the distance of the total width.

3. A tissue product as defined in claim 1, further comprising a second bonding material applied to the second side of the tissue web in a pattern, the pattern also comprising a plurality of individual cells, each cell comprising first and second expanded regions connected together by a constricted region.

4. A tissue product as defined in claim 3, wherein the second side of the tissue web has been creped after application of the second bonding material.

5. A tissue product as defined in claim 1, wherein the bonding material comprises an ethylene vinyl acetate copolymer.

6. A tissue product as defined in claim 1, wherein the expanded regions of the individual cells have a square, triangular, hexagonal, curvilinear, or elliptical shape.

7. A tissue product as defined in claim 1, wherein the constricted regions of the individual cells have a width that is less than the length of the average length of the pulp fibers contained in the tissue sheet.

8. A tissue product as defined in claim 1, wherein the constricted regions of the individual cells have a width that is less than about 2 mm.

9. A tissue product as defined in claim 1, wherein the constricted regions of the individual cells have a width that is less than about 1 mm.

10. A tissue product as defined in claim 1, wherein the individual cells of the pattern are interconnected along at least two sides of each cell.

11. A tissue product as defined in claim 1, wherein the individual cells of the pattern are interconnected along all sides of each cell.

12. A tissue product as defined in claim 1, wherein the pulp fibers comprise softwood fibers.

13. A tissue product as defined in claim 1, wherein the tissue web comprises an uncreped through-air dried web prior to application of the bonding material.

14. A tissue product as defined in claim 1, wherein the pattern by which the bonding material has been applied to the first side of the tissue web covers from about 30% to about 80% of the surface area of the web.

15. A tissue product as defined in claim 1, wherein the bonding material is applied to the first side of the tissue web in an amount from about 4% to about 10% by weight of the web.

16. A tissue product as defined in claim 1, wherein the tissue product has a bulk greater than about 5 cc/g.

17. A tissue product as defined in claim 1, wherein the tissue product has a bulk greater than about 9 cc/g.

18. A tissue product as defined in claim 1, wherein the bonding material is applied to the tissue web in a pattern that extends in the machine direction of the web and wherein when the tissue web is stretched in the machine direction, the constricted regions of the individual cells expand.

19. A tissue product as defined in claim 4, wherein the expanded regions of the individual cells have a square, triangular, hexagonal, curvilinear, or elliptical shape.

20. A tissue product as defined in claim 4, wherein the constricted regions of the individual cells have a width that is less than about 1 mm.

21. A tissue product as defined in claim 4, wherein the individual cells of the pattern are interconnected along all sides of each cell.

22. A tissue product as defined in claim 4, wherein the pattern applied to the first side of the tissue web and the pattern applied to the second side of the tissue web are substantially identical.

23. A tissue product as defined in claim 1, wherein the constricted regions of the individual cells have a width of from about 0.3 mm to about 1 mm.

24. A tissue product as defined in claim 1, wherein the constricted regions of the individual cells have a width of from about 0.5 mm to about 0.8 mm.

25. A tissue product as defined in claim 1, wherein the tissue web comprises a wet-creped web.

26. A tissue product as defined in claim 4, wherein the tissue web comprises a wet-creped web.

27. A tissue product comprising:
   a tissue web containing pulp fibers, the pulp fibers comprising softwood fibers, the tissue web having a first side and a second side, said tissue web defining a width direction and a length direction;
   a first bonding material applied to the first side of the tissue web in a first pattern, the first pattern comprising a plurality of individual cells, each cell comprising first and second expanded regions connected together by a constricted region having a width of less than about 1 mm, the pattern being interconnected such that at least two sides of each individual cell are interconnected to adjacent cells;

a second bonding material applied to the second side of the tissue web in a second pattern, the second pattern also comprising a plurality of individual cells, each cell comprising first and second expanded regions connected together by a constricted region having a width of less than about 1 mm, the second pattern being interconnected such that at least two sides of each individual cell are interconnected to adjacent cells;

wherein both sides of the tissue web have been creped after application of the bonding material; and wherein the tissue product has a basis weight of from about 10 gsm to about 80 gsm, the tissue product having a Poisson ratio of the width and length directions of less than about 0.3.

28. A tissue product as defined in claim 27, wherein the pattern extends in the machine direction and wherein the tissue web has a Poisson ratio of less than about 0.25.

29. A tissue product as defined in claim 27, wherein the pattern extends in the machine direction and wherein the tissue web has a Poisson ratio of less than about 0.1.

30. A tissue product as defined in claim 27, wherein the pattern extends in the machine direction and wherein the tissue web has a negative Poisson ratio.

31. A tissue product as defined in claim 27, wherein the tissue web comprises a wet-creped web.

32. A tissue product as defined in claim 27, wherein the expanded regions of the individual cells have a square, triangular, hexagonal, curvilinear, or elliptical shape.

33. A tissue product as defined in claim 27, wherein the individual cells of the pattern are interconnected along all sides of each cell.

34. A tissue product as defined in claim 27, wherein the tissue web comprises an uncreped through-air dried web prior to application of the bonding material.

35. A tissue product as defined in claim 27, wherein the first and second patterns cover from about 30% to about 80% of the surface area of each side of the tissue web.

36. A tissue product as defined in claim 27, wherein the bonding material is applied to the tissue web in a pattern that extends in the machine direction of the web and wherein when the tissue web is stretched in the machine direction, the constricted regions of the individual cells expand.

37. A method for producing a tissue product comprising:
providing a tissue web comprising pulp fibers, the tissue web having a first side and second side, said tissue web defining a width direction and a length direction wherein said tissue web has a Poisson ratio of the width and length directions;

applying a first bonding material to the first side of the web in a preselected pattern, the pattern comprising a plurality of individual cells, each cell comprising first and second expanded regions connected together by a constricted region, wherein said pattern reduces the Poisson ratio of said tissue web;

adhering the first side of the web to a creping surface; and creping the first side of the web from the creping surface.

38. A method as defined in claim 37, wherein a second bonding material is applied to the second side of the web in a second preselected pattern, the second pattern also comprising a plurality of individual cells, each cell comprising first and second expanded regions connected together by a constricted region.

39. A method as defined in claim 37, wherein the resulting tissue product has a Poisson ratio of less than about 0.3.

40. A method as defined in claim 37, wherein the resulting tissue product has a Poisson ratio of less than about 0.1.

41. A method as defined in claim 37, wherein the expanded regions of the individual cells have a square, triangular, hexagonal, curvilinear, or elliptical shape.

42. A method as defined in claim 37, wherein the constricted regions have a width of less than about 1 mm.

43. A method as defined in claim 37, wherein the constricted regions have a width of from about 0.3 mm to about 0.8 mm.

44. A method as defined in claim 37, wherein the individual cells contained in the pattern are interconnected.

45. A method as defined in claim 37, wherein the tissue product has a basis weight of from about 20 gsm to about 80 gsm and has a bulk of greater than about 9 cc/g, the bonding material being applied to the first side of the web in an amount of from about 4% to about 10% by weight of the web.

46. A method as defined in claim 37, wherein the tissue web has a length and a width and wherein the width shrinks less than 1.5% during creping.

* * * * *